United States Patent
Carniato et al.

(10) Patent No.: US 8,673,955 B2
(45) Date of Patent: Mar. 18, 2014

(54) IMIDAZOLE DERIVATIVES AS FRUCTOSE-1,6-BISPHOSPHATASE INHIBITORS AND PHARMACEUTICAL COMPOSITIONS CONTAINING THEM

(75) Inventors: Denis Carniato, Marcoussis (FR); Gérard Moinet, Orsay (FR); Gérard Botton, Buc (FR); Annick Arbellot De Vacqueur, Fontenay les Briis (FR); Annick Audet, Leudeville (FR)

(73) Assignee: Merck Patent GmbH, Darmstadt (DE)

( * ) Notice: Subject to any disclaimer, the term of this patent is extended or adjusted under 35 U.S.C. 154(b) by 1386 days.

(21) Appl. No.: 11/997,485

(22) PCT Filed: Jul. 19, 2006

(86) PCT No.: PCT/EP2006/007104
§ 371 (c)(1),
(2), (4) Date: Jan. 31, 2008

(87) PCT Pub. No.: WO2007/019937
PCT Pub. Date: Feb. 22, 2007

(65) Prior Publication Data
US 2008/0312299 A1    Dec. 18, 2008

(30) Foreign Application Priority Data
Aug. 1, 2005  (EP) .................... 05291641

(51) Int. Cl.
| | | |
|---|---|---|
| A61K 31/4439 | (2006.01) | |
| A61K 31/4245 | (2006.01) | |
| A61K 31/4178 | (2006.01) | |
| A61K 31/4164 | (2006.01) | |
| C07D 413/12 | (2006.01) | |
| C07D 409/04 | (2006.01) | |
| C07D 413/14 | (2006.01) | |
| C07D 233/64 | (2006.01) | |

(52) U.S. Cl.
USPC ........... 514/400; 514/397; 514/364; 514/341; 548/315.4; 548/315.1; 548/341.1; 548/335.5; 548/131; 546/275.1; 546/272.7

(58) Field of Classification Search
USPC .............. 514/400, 397, 364, 341; 546/275.1, 546/272.7; 548/315.4, 315.1, 341.1, 335.5, 548/131
See application file for complete search history.

(56) References Cited

U.S. PATENT DOCUMENTS
5,658,889 A    8/1997  Gruber et al.

FOREIGN PATENT DOCUMENTS
WO    WO 92/10183 A1    6/1992

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Hill et al. Bioorganic & Medicinal Chemistry Letters, 1995, 5, 19-24.*

* cited by examiner

*Primary Examiner* — Joseph Kosack
*Assistant Examiner* — Matthew Coughlin
(74) *Attorney, Agent, or Firm* — Millen, White, Zelano & Branigan, P.C.

(57) ABSTRACT

Imidazole derivatives of formula (I):

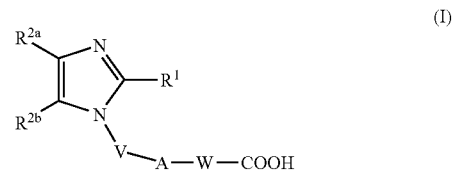

wherein $R^1$, $R^{2a}$, $R^{2b}$, A, V and W are as defined in the description,
as inhibitors of fructose-1,6-bisphosphatase,
their preparation process and
their use in the prevention or treatment of diabetes, and other diseases where the inhibition of gluconeogenesis, control of blood glucose levels, reduction in glycogen stores, or reduction in insulin levels is beneficial and diseases related to the insulin resistance syndrome.

16 Claims, 3 Drawing Sheets

Scheme 1:

Scheme 2:

Scheme 3:

IMIDAZOLE DERIVATIVES AS FRUCTOSE-1,6-BISPHOSPHATASE INHIBITORS AND PHARMACEUTICAL COMPOSITIONS CONTAINING THEM

FIELD OF THE INVENTION

This invention relates to novel imidazole derivatives that are inhibitors of fructose-1,6-bisphosphatase. The invention also relates to the preparation and use of these benzimidazole derivatives in the treatment of diabetes, and other diseases where the inhibition of gluconeogenesis, control of blood glucose levels, reduction in glycogen stores, or reduction in insulin levels is beneficial and diseases related to the insulin resistance syndrome.

BACKGROUND AND INTRODUCTION TO THE INVENTION

Diabetes mellitus (or diabetes) is one of the most prevalent diseases in the world today. Diabetes patients have been divided into two classes, namely type I or insulin-dependent diabetes mellitus and type II or non-insulin dependent diabetes mellitus (NIDDM). Non-insulin-dependent diabetes mellitus (NIDDM) accounts for approximately 90% of all diabetics and is estimated to affect 12-14 million adults in the U.S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term complications and hyperglycemia. Recent results from the Diabetes Control and Complications Trial (DCCT) and the Stockholm Prospective Study demonstrate this relationship for the first time in man by showing that insulin-dependent diabetics with tighter glycogenic control are at substantially lower risk for development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese (≈67%) and since weight loss can improve insulin secretion, insulin sensitivity and lead to normoglycaemia. Normalization of blood glucose occurs in less than 30% of these patients due to poor compliance and poor response. Patients with hyperglycemia not controlled by diet alone are subsequently treated with oral hypoglycaemics or insulin. Today, insulin secretagogues (sulfonylureas, glinides), biguanides (metformin) and insulin sensitizers (glitazone) are the only class of oral hypoglycemic agents available for NIDDM. Treatment with sulfonylureas leads to effective blood glucose lowering in only 70% of patients and only 40% after 10 years of therapy. Patients that fail to respond to diet and sulfonylureas are subsequently treated with daily insulin injections to gain adequate glycogenic control.

Although the sulfonylureas represent a major therapy for NIDDM patients, four factors limit their overall success. First, as mentioned above, a large segment of the NIDDM population does not respond adequately to sulfonylurea therapy (i.e. primary failures) or become resistant (i.e. secondary failures). This is particularly true in NIDDM patients with advanced NIDDM since these patients have severely impaired insulin secretion. Second, sulfonylurea therapy is associated with an increased risk of severe hypoglycemic episodes. Third, chronic hyperinsulinemia has been associated with increased cardiovascular disease although this relationship is considered controversial and unproven. Last, sulfonylureas are associated with weight gain, which leads to worsening of peripheral insulin sensitivity and thereby can accelerate the progression of the disease.

Recent results from the U.K. Diabetes prospective study also showed that patients undergoing maximal therapy of a sulfonylurea, metformin, or a combination of the two, were unable to maintain normal fasting glycaemia over the six year period of the study. U.K. Prospective Diabetes Study 16. *Diabetes*, 44:1249-158 (1995). These results further illustrate the great need for alternative therapies. Three therapeutic strategies that could provide additional health benefits to NIDDM patients beyond the currently available therapies, include drugs that would: (i) prevent the onset of NIDDM; (ii) prevent diabetic complications by blocking detrimental events precipitated by chronic hyperglycemia; or (iii) normalize glucose levels or at least decrease glucose levels below the threshold reported for microvascular and macrovascular diseases.

Hyperglycemia in NIDDM is associated with two biochemical abnormalities, namely insulin resistance and impaired insulin secretion. The relative roles of these metabolic abnormalities in the pathogenesis of NIDDM have been the subject of numerous studies over the past several decades. Studies of offspring and siblings of NIDDM patients, mono- and dizygotic twins, and ethnic populations with high incidence of NIDDM (e.g. Pima Indians) strongly support the inheritable nature of the disease.

Despite the presence of insulin resistance and impaired insulin secretion, fasting blood glucose (FBG) levels remain normal in pre-diabetic patients due to a state of compensatory hyperinsulinemia. Eventually, however, insulin secretion is inadequate and fasting hyperglycemia ensues. With time insulin levels decline. Progression of the disease is characterized by increasing FBG levels and declining insulin levels.

Numerous clinical studies have attempted to define the primary defect that accounts for the progressive increase in FBG. Results from these studies indicate that excessive hepatic glucose output (HGO) is the primary reason for the elevation in FBG with a significant correlation found for HGO and FBG once FBG exceeds 140 mg/dL. Kolterman, et al., *J. Clin. Invest.* 68:957, (1981); DeFronzo *Diabetes* 37:667 (1988).

HGO comprises glucose derived from breakdown of hepatic glycogen (glycogenolysis) and glucose synthesized from 3-carbon precursors (gluconeogenesis). A number of radioisotope studies and several studies using $^{13}$C-NMR spectroscopy have shown that gluconeogenesis contributes between 50-100% of the glucose produced by the liver in the postabsorptive state and that gluconeogenesis flux is excessive (2- to 3-fold) in NIDDM patients. Magnusson, et al. *J. Clin. Invest.* 90:1323-1327 (1992); Rothman, et al., *Science* 254: 573-76 (1991); Consoli, et al. *Diabetes* 38:550-557 (1989).

Gluconeogenesis from pyruvate is a highly regulated biosynthetic pathway requiring eleven enzymes (FIG. 1). Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase and glucose-6-phosphatase. Overall flux through the pathway is controlled by the specific activities of these enzymes, the enzymes that catalyzed the corresponding steps in the glycolytic direction, and by substrate availability. Dietary factors (glucose, fat) and hormones (insulin, glucagon, glucocorticoids, epinephrine) coordinatively regulate enzyme activities in the gluconeogenesis and glycolysis pathways through gene expression and post-translational mechanisms.

Of the four enzymes specific to gluconeogenesis, fructose-1,6-bisphosphatase (hereinafter "FBPase") is a very suitable target for a gluconeogenesis inhibitor based on efficacy and safety considerations. Studies indicate that nature uses the FBPase/PFK cycle as a major control point (metabolic switch) responsible for determining whether metabolic flux proceeds in the direction of glycolysis or gluconeogenesis. Claus, et al., *Mechanisms of Insulin Action*, Belfrage, P. editor, pp. 305-321, Elsevier Science 1992; Regen, et al., *J. Theor. Biol.*, 111:635-658 (1984); Pilkis, et al., *Annu. Rev. Biochem*, 57:755-783 (1988). FBPase is inhibited by fructose-2,6-bisphosphate in the cell. Fructose-2,6-bisphosphate binds to the substrate site of the enzyme. AMP binds to an allosteric site on the enzyme.

Synthetic inhibitors of FBPase have also been reported. Maryanoff reported that fructose-2,6-bisposphate analogs inhibit FBPase by binding to the substrate. *J. Med. Chem.*, 106:7851 (1984); U.S. Pat. No. 4,968,790 (1984). These compounds, however, were relatively weak and did not inhibit glucose production in hepatocytes presumably due to poor cell penetration.

Several inhibitors of fructose-1,6-bisphosphatase useful for treating diabetes have been reported:

Gruber reported that some nucleosides can lower blood glucose in the whole animal through inhibition of FBPase (EP 0 427 799 B1). These compounds exert their activity by first undergoing phosphorylation to the corresponding monophosphate;

Gruber et al. U.S. Pat. No. 5,658,889 described the use of inhibitors of the AMP site of FBPase to treat diabetes;

Dan et al. (WO 98/39344, WO 00/014095) described novel purines and heroaromatics as inhibitors of FBPase;

Kasibhatla et al. (WO 98/39343) described novel benzimidazolyl-phosphonates as inhibitors of FBPase;

Reddy et al. (WO 98/39342) described novel indoles and aza-indoles as inhibitors of FBPase;

Jaing et al. (WO 01/047935) describe bisamidate phosphonates as specific inhibitors of FBPase to treat diabetes;

Bookser et al. (WO01/066553) describes arylherterocycle phosphates as specific inhibitors of FBPase to treat diabetes.

Imidazolylalkanoic acid derivatives have already been described (WO 93/03722, JP-05201991, JP-06025229, EP 0 253 310, EP 0 324 377, EP 0 465 368, WO 92/02510, EP 0 564 356, *J. Org. Chem.*, (1997), 62(64), p. 8449-8454, *J. Med. Chem.*, (1990), 33(5), p. 1312-1329) as angiotensin II receptor antagonists.

SUMMARY OF THE INVENTION

The present invention is directed towards novel imidazole derivatives as potent FBPase inhibitors useful for treating diabetes and related diseases.

More precisely the invention is related to imidazole derivatives of formula (I):

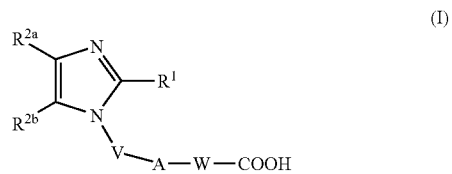

wherein:
$R^1$ is chosen from among hydrogen, $(C_1-C_6)$alkyl, $(C_3-C_{10})$ cycloalkyl, aryl, heteroaryl, heterocycloalkyl, aralkyl and heteroaralkyl;
$R^{2a}$ and $R^{2b}$ are dependent and are such that:
    either $R^{2a}$ represents —$CH_2$—X—Z—B and $R^{2b}$ is chosen from among hydrogen and $(C_1-C_6)$alkyl;
    or $R^{2a}$ is chosen from among hydrogen and $(C_1-C_6)$alkyl and $R^{2b}$ represents —$CH_2$—X—Z—B and;
A is a divalent radical chosen from among aryl, heteroaryl, aralkyl and heteroaralkyl after removal of one hydrogen atom;
B is chosen from among aryl, heteroaryl, aralkyl and heteroaralkyl;
V and W, independently from one another, each represent a single bond or are chosen from among alkylene, alkyleneoxyalkylene, alkenylene and alkynylene;
X is chosen from among —NR—, —O—, —S—, —SO— and —$SO_2$—, with R being hydrogen or $(C_1-C_6)$alkyl;
Z represents —$(CH_2)_m$—, with m being 1, 2, 3, 4, 5 or 6.

Since these compounds may have asymmetric centers, the present invention is directed not only to racemic mixtures of these compounds, but also to individual stereoisomers and/or diastereoisomers thereof as well as mixtures of these in all proportions. The present invention also includes pharmaceutically acceptable and/or useful salts of the compounds of formula (I), including acid addition salts. The present invention also includes solvates and oxides, especially N-oxides. The present inventions also encompass prodrugs of compounds of formula (I). All compounds encompassed by the present invention may exist in the solid form, such as crystals, including their polymorphic forms.

The acids used for the preparation of the pharmaceutically acceptable salts are inorganic or organic acids. The resulting salts are for example hydrochlorides, hydrobromides, sulfates, hydrogenosulfates, dihydrogeno-phosphates, citrates, maleates, fumarates, trifluoroacetates, 2-naphtalenesulfonates, para-toluenesulfonates.

The invention also relates to pharmaceutically acceptable salts with organic or inorganic bases. The resulting salts are for example metal salts, particularly alkali metal salts, alkaline-earth metal salts and transition metal salts (such as sodium, potassium, calcium, magnesium, aluminum) or salts obtained with bases such as ammoniac or secondary or tertiary amines (such as diethylamine, triethylamine, piperidine, piperazine, morpholine) or with basic amino-acids, or with osamines (such as meglumine) or with amino-alcohols (such as 3-aminobutanol and 2-aminoethanol).

The invention also relates to the salts used for chiral resolution of the racemates.

As examples the following chiral acids can be used: (+)-D-di-O-benzoyltartaric acid, (−)-L-di-O-benzoyltartaric acid, (−)-L-di-O,O'-p-toluoyl-L-tartaric acid, (+)-D-di-O,O'-p-toluoyl-L-tartaric acid, (R)-(+)-malic acid, (S)-(−)-malic acid, (+)-camphoric acid, (−)-camphoric acid, R-(+1,1'-binaphtalen-2,2'-diyl hydrogenophosphonic, (+)-camphanic acid, (−)-camphanic acid, (S)-(+)-2-phenylpropionic acid, (R)-(+)-

2-phenylpropionic acid, D-(−)-mandelic acid, L-(+)-mandelic acid, D-tartaric acid, L-tartaric acid, or any mixture of them.

As examples the following chiral amines can be used: quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethyl-amine, (S)-phenylglycinol, (−)-N-methylephedrine, (+)-(2S,3R)-4-dimethylamino-3-methyl-1,2-diphenyl-2-butanol, (S)-phenylglycinol, (S)-α-methylbenzylamine or any mixture of them.

Also included in the scope of the present invention are prodrugs of the compounds of formula (I).

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s). Standard prodrugs are formed using groups attached to functionality, e.g. hydroxyl, thiol, carboxy, amino, alkylamino, dialkylamino, associated with the FBPase inhibitor, that cleave in vivo.

Standard prodrugs include but are not limited to carboxylate esters where the ester group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Prodrugs must undergo some form of a chemical transformation to produce the compound that is biologically active or is a precursor of the biologically active compound. In some cases, the prodrug is biologically active usually less than the drug itself, and serves to improve efficacy or safety through improved oral bioavailability, pharmacodynamic half-life, etc.

In accordance with the present invention and as used herein, the following terms are defined with the following meanings, unless explicitly stated otherwise.

The term "aryl" refers to aromatic groups which have 5-14 ring atoms and at least one ring having a conjugated pi (π) electron system and includes biaryl groups, all of which may be optionally substituted. Suitable aryl groups include biphenyl, phenyl, naphthyl, anthryl, phenanthryl, and the like, all optionally substituted.

The term "heteroaryl" refers to 5-14 ring atom aromatic heterocycles containing 1 to 4 heteroatoms as ring atoms in the aromatic ring and the remainder of the ring atoms being carbon atoms. Suitable heteroatoms include oxygen, sulfur, nitrogen. Suitable heteroaryl groups include furanyl, thienyl, pyridyl, pyrrolyl, N-lower alkyl, pyridyl-N-oxide, pyrimidyl, pyrazinyl, imidazolyl, oxazolyl, oxadiazolyl, quinolinyl, thiazolyl, triazolyl and the like, all optionally substituted.

The term "heterocycloalkyl" refers to optionally substituted monocyclic, bicyclic or tricyclic radicals comprising one or more heteroatoms, preferably chosen from among O, S and N, optionally in the oxidized state (for S and N), and optionally one or more double bonds. At least one of the rings preferably comprises from 1 to 4 endocyclic heteroatoms, more preferably from 1 to 3 heteroatoms.

Most preferably, the heterocycloalkyl (or simply "heterocyclic") radical comprises one or more rings, each having from 5 to 8 nodes. Examples of heterocyclic radicals are morpholinyl, piperidinyl, thiazolidinyl, oxazolidinyl, tetrahydrothienyl, tetrahydrofuranyl, pyrrolidinyl, isoxazolidinyl, imidazolidinyl or pyrazolidinyl.

The term "($C_3$-$C_{10}$)cycloalkyl" means saturated carbocyclic rings and includes mono-, bi- and poly-cyclic compounds with 3 to 10 carbon atoms. Suitable cycloalkyl groups are cyclopropyl, cyclobutyl, cyclopentyl, cyclohexyl, cycloheptyl, cyclooctyl or cyclodecyl and the like, all optionally substituted.

The term "optionally substituted" or "substituted" includes groups substituted by one to four substituents, independently selected from lower alkyl, lower aryl, lower aralkyl, lower cycloalkyl or heterocycloalkyl, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, carbonylamino, carboxamido, nitro, acyloxy, aminoalkyl, alkylaminoaryl, alkylaryl, alkylaminoalkyl, alkoxyaryl, arylamino, aralkylamino, phosphono, sulfonyl, carboxamidoalkylaryl, carboxamidoaryl, hydroxyalkyl, halo, haloalkyl, alkylaminoalkylcarbonyl, aminocarboxamidoalkyl, cyano, lower alkoxyalkyl, lower perhaloalkyl, perhaloalkoxy, and arylalkyloxyalkyl.

The terms "substituted aryl" and "substituted heteroaryl" preferably refer to aryl and heteroaryl groups substituted with 1-3 substituents. Preferably these substituents are selected from the group consisting of lower alkyl, lower alkoxy, lower perhaloalkyl, halo, hydroxy, and amino.

The term "aralkyl" refers to an alkyl group substituted with an aryl group. Suitable aralkyl groups include benzyl, picolyl, and the like, and may be optionally substituted.

The term "heteroarylalkyl" refers to an alkyl group substituted with a heteroaryl group.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NR'R" wherein respectively, (a) R' is aryl and R" is hydrogen, alkyl, aralkyl or aryl, and (b) R' is aralkyl and R" is hydrogen or aralkyl, aryl, alkyl.

The term "acyl" refers to —C(O)R'" where R'" is alkyl and aryl.

The term "carboxy esters" refers to —C(O)OR"" where R"" is alkyl, aryl, aralkyl, cycloalkyl and heterocycloalkyl, all optionally substituted.

The term "carboxyl" refers to —C(O)OH.

The term "oxo" refers to =O in an alkyl group.

The term "amino" refers to —NR$^a$R$^b$ where R$^a$ and R$^b$ are independently selected from hydrogen, alkyl, aryl, heteroaryl, aralkyl, heteroaralkyl, cycloalkyl and heterocycloalkyl, all except hydrogen are optionally substituted; and R$^a$ and R$^b$ may together form a cyclic ring system.

The terms "carboxamido" and "carbonylamino" refer to —CONR$^a$R$^b$ and —NR$^a$C(O)R$^b$, respectively, where R$^a$ and R$^b$ being as defined above.

The term "halogen" or "halo" refers to —F, —Cl, —Br and —I.

The term "oxyalkylamino" refers to —O-alk-NR$^a$R$^b$, where "alk" is an alkylene group and R$^a$ and R$^b$ are as defined above.

The term "alkylaminoalkylcarbonyloxy" refers to the group -alk-NR-alk-C(O)—O— where "alk" is an alkylene group, and R is hydrogen or lower alkyl.

The term "alkylaminocarbonyl" refers to the group alk-NR—C(O)—where "alk" is an alkyl group, and R is a hydrogen or lower alkyl.

The term "oxyalkyl" refers to the group —O-alk where "alk" is an alkyl group.

The term "alkyleneoxyalkylene" refers to the group -Alk-O-Alk- where "Alk" is an alkylene group.

The term "alkylcarboxyalkyl" refers to the group -Alk-C(O)—O-Alk- where each Alk is independently an alkylene group.

The term "alkyl" refers to $C_1$-$C_{10}$ saturated aliphatic groups including straight chain and branched chain groups. Alkyl groups may be optionally substituted. Suitable alkyl groups include methyl, ethyl, propyl, isopropyl, butyl, isobutyl, tert-butyl, pentyl, isopentyl, neopentyl, methylbutyl, ethylpropyl, hexyl, isohexyl, neohexyl, methylpentyl, dimethylbutyl, methylethylpropyl and cyclopropyl.

The term "alkylene" refers to a divalent radial obtained from an alkyl radical after one hydrogen atom has been withdrawn.

The terms "alkenyl" and "alkenylene" refer to unsaturated groups comprising at least one carbon-carbon double bond and includes straight chain, branched chain and cyclic groups.

The terms "alkynyl" and "alkynylene" refer to unsaturated groups comprising at least one carbon-carbon triple bond and includes straight chain, branched chain and cyclic groups.

The term "sulfonyl" refers to —$SO_3R$, where R is hydrogen, alkyl, aryl, aralkyl, and cycloalkyl.

The term "acyloxy" refers to the ester group —O—C(O)R, where R is hydrogen, alkyl, alkenyl, alkynyl, aryl, aralkyl, or cycloalkyl.

The term "aminoalkyl" refers to the group $NR^aR^b$-Alk- wherein "Alk" is an alkylene group and $R^a$ and $R^b$ are as defined above.

The term "alkylaminoalkyl" refers to the group alkyl-$NR^a$-Alk- wherein "Alk" is alkylene, and $R^a$ is as defined above.

The term "arylaminoalkyl" refers to the group aryl-$NR^a$-Alk- wherein "Alk" is alkylene, and $R^a$ is as defined above.

The term "alkylaminoaryl" refers to the group alkyl-$NR^a$-aryl- wherein "aryl" is a divalent arylene group and $R^a$ is as defined above.

The term "alkyloxyaryl" refers to an aryl group substituted with an alkyloxy group.

The term "aryloxyalkyl" refers to an alkyl group substituted with an aryloxy group.

The term "aralkyloxyalkyl" refers to the group aryl-Alk-O-Alk- wherein "Alk" is an alkylene group. "Lower aralkyloxyalkyl" refers to such groups where the alkylene groups are lower alkylene.

The term "alkoxy" or "alkyloxy" refers to the group alk-O— wherein "alk" is an alkyl group.

The term "alkoxyalkyl-" or "alkyloxyalkyl-" refers to the group alk-O-Alk- wherein "alk" is an alkyl group and "Alk" is an alkylene group.

The terms "alkylthio" refers to the group alkyl-S—, wherein "alk" is an alkyl group.

The term "alkylthioalkyl-" refers to the group alk-S-Alk- wherein "alk" is an alkyl group and "Alk" is an alkylene group.

The term "alkoxycarbonyloxy" refers to alkyl-O—C(O)—O—.

The term "aryloxycarbonyloxy" refers to aryl-O—C(O)—O—.

The term "alkylthiocarbonyloxy" refers to alkyl-S—C(O)—O—.

The term "alkoxycarbonylamino" refers to alkyl-O—C(O)—NR—, where R is as defined above.

The term "alkylaminocarbonylamino-" refers to alkyl-NR—C(O)—NR—, where each R is independently selected from hydrogen, alkyl, aryl, aralkyl, and cycloalkyl.

The terms "amido" and "carboxamido" refer to N($R^aR^b$)—C(O)— and RC(O)—$NR^c$—, where $R^a$ and $R^b$ are as defined above and $R^c$ has the same definition as for $R^a$ or $R^b$. The term does not include urea, —NR—C(O)—NR—.

The terms "carboxamidoalkylaryl" and "carboxamidoaryl" refer to aryl-Alk-$NR^c$—C(O)—, and aryl-$NR^c$—C(O)—, respectively, where "Alk" is alkylene, and $R^c$ is as defined above.

The term "alkylcarboxamido" or "alkylcarbonylamino" refers to the group alk-C(O)N($R^c$)—, wherein "alk" is an alkyl group and $R^c$ is as defined above.

The term "alkylaminocarbonyl" refers to the group alkyl-$NR^c$—C(O)— wherein $R^c$ is as defined above.

The term "aminocarboxamidoalkyl" refers to the group N($R^aR^b$)—C(O)—N($R^c$)-Alk- wherein $R^a$, $R^b$ and $R^c$ are as defined above and "Alk" is an alkylene group. "Lower aminocarboxamidoalkyl" refers to such groups wherein "Alk" is lower alkylene.

The term "thiocarbonate" refers to —O—C(S)—O— either in a chain or in a cyclic group.

The term "hydroxyalkyl" refers to an alkyl group substituted with one —OH.

The term "haloalkyl" refers to an alkyl group substituted with one halo, selected from the group I, Cl, Br and F.

The term "cyano" refers to —C≡N.

The term "nitro" refers to —$NO_2$.

The term "acylalkyl" refers to an alkyl-C(O)-Alk-, where "Alk" is alkylene.

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —$CF_3$ and —$CFCl_2$.

The term "guanidino" refers to both —$NR^c$—C(NR)—$NR^aR^b$ as well as —N=C($NR^aR^b$)$_2$ where $R^a$, $R^b$ and $R^c$ are as defined above, all except hydrogen are optionally substituted.

The term "amidino" refers to —C($NR^c$)—$NR^aR^b$ where $R^a$, $R^b$ and $R^c$ are as defined above, all except hydrogen are optionally substituted.

A preferred embodiment of the invention relates to compounds of formula (I) and wherein:
$R^1$ is chosen from among hydrogen, aryl and heteroaryl;
$R^{2a}$ represents —$CH_2$—X—Z—B and $R^{2b}$ represents hydrogen or lower alkyl; or
$R^{2b}$ represents —$CH_2$—X—Z—B and $R^{2a}$ represents hydrogen or lower alkyl;
A represents a bivalent radical ($A^1$) or ($A^2$):

(A$^1$)

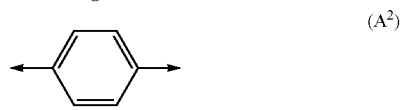

(A$^2$)

B is chosen from among aryl, heteroaryl, aralkyl and heteroaralkyl;
represents —$CH_2$—;
W represents a single bond;
X represents —O—; and
Z represents —$CH_2$—.

In an other preferred embodiment the invention relates to compounds of formula (I) wherein:

$R^1$ is chosen from among hydrogen, aryl and heteroaryl;

$R^{2a}$ represents —$CH_2$—X—Z—B and $R^{2b}$ represents hydrogen or lower alkyl; or $R^{2b}$ represents —$CH_2$—X—Z—B and $R^{ea}$ represents hydrogen or lower alkyl;

B is chosen from the following $B^1$-$B^5$ radicals:

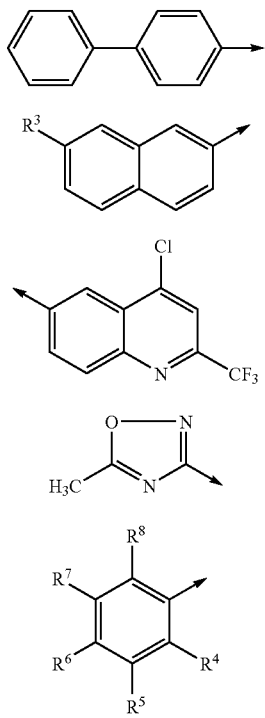

where each of $R^3$ to $R^8$ is independently chosen from the "substituents" as defined above, A represents a bivalent radical ($A^1$) or ($A^2$):

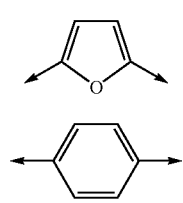

represents —$CH_2$—;
W represents a single bond;
X represents —O—; and
Z represents —$CH_2$—.

In an other preferred embodiment the invention relates to compounds of formula (I) wherein:

$R^1$ is chosen from among hydrogen, aryl and heteroaryl;

$R^{2a}$ represents —$CH_2$—X—Z—B and $R^{2b}$ represents hydrogen or lower alkyl; or $R^{2b}$ represents —$CH_2$—X—Z—B and $R^{2a}$ represents hydrogen or lower alkyl;

B is chosen from among the $B^1$-$B^5$ radicals as defined above, wherein:

$R^3$ represents the following radical:

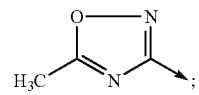

$R^4$, $R^5$, $R^6$, $R^7$ and $R^8$ are each independently from one another chosen from among hydrogen, Cl, Br, F, $CF_3$, CN, $CH_3$, $CH_3O$, tert-butyl and the radical of formula:

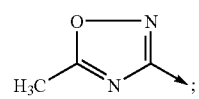

A represents a bivalent radical ($A^1$) or ($A^2$) as defined above;
represents —$CH_2$—;
W represents a single bond;
X represents —O—; and
Z represents —$CH_2$—.

In an other preferred embodiment the invention relates to compounds of formula (I) wherein:

$R^1$ is chosen form among hydrogen, and either radical $R^{1a}$ or $R^{1b}$:

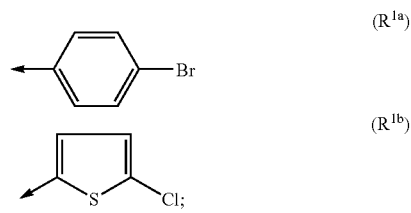

$R^{2a}$ represents —$CH_2$—X—Z—B and $R^{2b}$ represents hydrogen or lower alkyl; or $R^{2b}$ represents —$CH_2$—X—Z—B and $R^{2a}$ represents hydrogen or lower alkyl;

B is chosen from among the $B^1$-$B^5$ radicals as defined above, wherein:

$R^3$ represents the following radical:

$R^4$, $R^5$, $R^6$, $R^7$ and $R^8$ are each independently from one another chosen from among hydrogen, Cl, Br, F, $CF_3$, CN, $CH_3$, $CH_3O$, tert-butyl and the radical of formula:

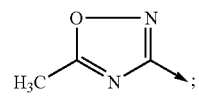

A represents a bivalent radical ($A^1$) or ($A^2$) as defined above;
V represents —$CH_2$—;
W represents a single bond;

X represents —O—; and
Z represents —CH$_2$—.

According to the above embodiments a preferred group of compounds is:

4-[5-(Biphenyl-4-ylmethoxymethyl)imidazol-1-ylmethyl]benzoic acid;
4-[5-(Biphenyl-4-ylmethoxymethyl)-4-methylimidazol-1-ylmethyl]benzoic acid;
4-[4-(Biphenyl-4-ylmethoxymethyl)imidazol-1-ylmethyl]benzoic acid;
4-[4-(Biphenyl-4-ylmethoxymethyl)-5-methylimidazol-1-ylmethyl]benzoic acid;
5-[5-(Biphenyl-4-ylmethoxymethyl)-5-methylimidazol-1-ylmethyl]-furan-2-carboxylic acid;
5-[5-(Biphenyl-4-ylmethoxymethyl)-4-methylimidazol-1-ylmethyl]furan-2-carboxylic acid;
4-(4-Benzyloxymethylimidazol-1-ylmethyl)benzoic acid;
4-[4-(4-Methylbenzyloxymethyl)imidazol-1-ylmethyl]benzoic acid;
4-[4-(4-tert-Butylbenzyloxymethyl)imidazol-1-ylmethyl]benzoic acid;
4-[4-(Naphthalen-2-ylmethoxymethyl)imidazol-1-ylmethyl]benzoic acid;
4-[4-(3-Fluorobenzyloxymethyl)imidazol-1-ylmethyl]benzoic acid;
4-[4-(3-Bromobenzyloxymethyl)imidazol-1-ylmethyl]benzoic acid;
4-[4-(3-Methoxybenzyloxymethyl)imidazol-1-ylmethyl]benzoic acid;
4-[4-(2,4-Difluorobenzyloxymethyl)imidazol-1-ylmethyl]benzoic acid;
4-[4-(2-Chloro-4-fluorobenzyloxymethyl)imidazol-1-ylmethyl]benzoic acid;
4-[4-(3,5-Dimethoxybenzyloxymethyl)imidazol-1-ylmethyl]benzoic acid;
4-[4-(3-Methylbenzyloxymethyl)imidazol-1-ylmethyl]benzoic acid;
4-[4-(3-Chlorobenzyloxymethyl)imidazol-1-ylmethyl]benzoic acid;
4-[4-(3-Trifluoromethylbenzyloxymethyl)imidazol-1-ylmethyl]benzoic acid;
4-[4-(Biphenyl-3-ylmethoxymethyl)-2-(5-chlorothiophen-2-yl)imidazol-1-ylmethyl]benzoic acid;
4-[2-(5-Chlorothiophen-2-yl)-4-(4-cyanobenzyloxymethyl)imidazol-1-ylmethyl]benzoic acid;
4-[2-(5-Chlorothiophen-2-yl)-4-(2,5-dichlorobenzyloxymethyl)imidazol-1-ylmethyl]benzoic acid;
4-[4-(4-Bromobenzyloxymethyl)-2-(5-chlorothiophen-2-yl)imidazol-1-ylmethyl]benzoic acid;
4-[4-(3-Chlorobenzyloxymethyl)-2-(5-chlorothiophen-2-yl)imidazol-1-ylmethyl]benzoic acid;
4-[2-(5-Chlorothiophen-2-yl)-4-(2-methylbenzyloxymethyl)imidazol-1-ylmethyl]benzoic acid;
4-{2-(5-Chlorothiophen-2-yl)-4-[7-(5-methyl-[1,2,4]oxadiazol-3-yl)-naphthalen-2-ylmethoxymethyl]imidazol-1-ylmethyl}benzoic acid;
4-{2-(5-Chlorothiophen-2-yl)-4-[2-(5-methyl-[1,2,4]oxadiazol-3-yl)benzyloxymethyl]imidazol-1-ylmethyl}benzoic acid;
4-[2-(5-Chlorothiophen-2-yl)-4-(3-cyanobenzyloxymethyl)imidazol-1-ylmethyl]benzoic acid;
4-[2-(5-Chlorothiophen-2-yl)-4-(2,6-difluorobenzyloxymethyl)imidazol-1-ylmethyl]benzoic acid;
4-[4-(2-Chlorobenzyloxymethyl)-2-(5-chlorothiophen-2-yl)imidazol-1-ylmethyl]benzoic acid;
4-[2-(5-Chlorothiophen-2-yl)-4-(2-fluorobenzyloxymethyl)imidazol-1-ylmethyl]benzoic acid;
4-[4-(4-Chlorobenzyloxymethyl)-2-(5-chlorothiophen-2-yl)imidazol-1-ylmethyl]benzoic acid;
4-[4-Benzyloxymethyl-2-(5-chlorothiophen-2-yl)imidazol-1-ylmethyl]benzoic acid;
4-[2-(5-Chlorothiophen-2-yl)-4-(3-methylbenzyloxymethyl)imidazol-1-ylmethyl]benzoic acid;
4-[2-(5-Chlorothiophen-2-yl)-4-(4-fluorobenzyloxymethyl)imidazol-1-ylmethyl]benzoic acid;
4-[2-(5-Chlorothiophen-2-yl)-4-(3-trifluoromethylbenzyloxymethyl)imidazol-1-ylmethyl]benzoic acid;
4-[2-(5-Chlorothiophen-2-yl)-4-(4-chloro-2-trifluoromethylquinolin-6-ylmethoxymethyl)imidazol-1-ylmethyl]benzoic acid;
4-[2-(5-Chlorothiophen-2-yl)-4-(2-cyanobenzyloxymethyl)imidazol-1-ylmethyl]benzoic acid;
4-[2-(5-Chlorothiophen-2-yl)-4-(naphthalen-2-ylmethoxymethyl)imidazol-1-ylmethyl]benzoic acid;
4-[2-(5-Chlorothiophen-2-yl)-4-(2-trifluoromethylbenzyloxymethyl)imidazol-1-ylmethyl]benzoic acid;
4-[2-(5-Chlorothiophen-2-yl)-4-(4-methylbenzyloxymethyl)imidazol-1-ylmethyl]benzoic acid;
4-[2-(4-Bromophenyl)-4-(2,5-dichlorobenzyloxymethyl)imidazol-1-ylmethyl]benzoic acid;
4-[4-(4-Bromobenzyloxymethyl)-2-(4-bromophenyl)-imidazol-1-ylmethyl]benzoic acid;
4-[2-(4-Bromophenyl)-4-(3-chlorobenzyloxymethyl)imidazol-1-ylmethyl]benzoic acid;
4-{2-(4-Bromophenyl)-4-[2-(5-methyl-[1,2,4]-oxadiazol-3-yl)benzyloxymethyl]imidazol-1-ylmethyl}benzoic acid;
4-[2-(4-Bromophenyl)-4-(2-cyanobenzyloxymethyl)imidazol-1-ylmethyl]benzoic acid;
4-[2-(4-Bromophenyl)-4-(4-chlorobenzyloxymethyl)imidazol-1-ylmethyl]benzoic acid;
4-[2-(4-Bromophenyl)-4-(3-methylbenzyloxymethyl)imidazol-1-ylmethyl]benzoic acid;
4-[2-(4-Bromophenyl)-4-(4-fluorobenzyloxymethyl)imidazol-1-ylmethyl]benzoic acid;
4-[4-(Biphenyl-3-ylmethoxymethyl)-2-(4-bromophenyl)imidazol-1-ylmethyl]benzoic acid;
4-[2-(4-Bromophenyl)-4-(4-cyanobenzyloxymethyl)imidazol-1-ylmethyl]benzoic acid;
4-[2-(4-Bromophenyl)-4-(naphthalen-2-ylmethoxymethyl)imidazol-1-ylmethyl]benzoic acid;
4-[2-(4-Bromophenyl)-4-(3-cyanobenzyloxymethyl)imidazol-1-ylmethyl]benzoic acid;
4-[2-(4-Bromophenyl)-4-(2-fluorobenzyloxymethyl)imidazol-1-ylmethyl]benzoic acid.

In an other preferred embodiment, the invention relates to the potassium salt of compounds of formula (I) wherein:
R$^1$ represents hydrogen;
R$^{2a}$ represents —CH$_2$—X—Z—B and R$^{2b}$ represents hydrogen; or
R$^{2b}$ represents —CH$_2$—X—Z—B and R$^{2a}$ represents hydrogen;
A represents:

B is chosen from among the following groups:

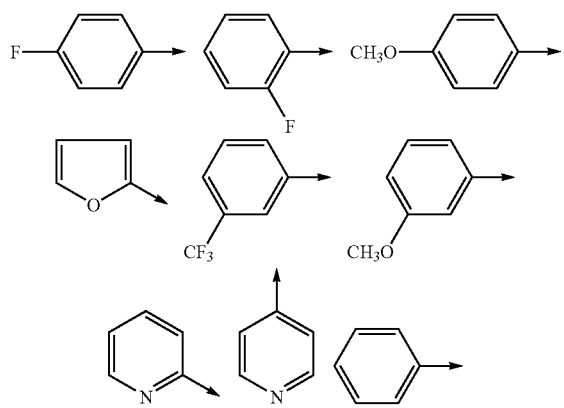

V represents —CH$_2$—;
W represents a single bond;
X represents —NH—; and
Z represents —CH$_2$—.

According to the above embodiment a preferred group of potassium salt compounds is:
Potassium, 4-{4-[(4-fluorobenzylamino)methyl]imidazol-1-ylmethyl}benzoate;
Potassium, 4-{4-[(3-methoxybenzylamino)methyl]imidazol-1-ylmethyl}benzoate;
Potassium, 4-{4-[(4-methoxybenzylamino)methyl]imidazol-1-ylmethyl}benzoate;
Potassium, 4-{4-[(3-trifluoromethylbenzylamino)methyl]imidazol-1-ylmethyl}benzoate;
Potassium, 4-{4-[(2-fluoro-4-bromobenzylamino)methyl]imidazol-1-ylmethyl}benzoate;
Potassium, 4-(4-{[(Furan-2-ylmethyl)amino]methyl}imidazol-1-ylmethyl)benzoate;
Potassium, 4-(4-{[(Pyridin-2-ylmethyl)amino]methyl}imidazol-1-ylmethyl)benzoate;
Potassium, 4-(4-{[(Pyridin-4-ylmethyl)amino]methyl}imidazol-1-ylmethyl)benzoate;
Potassium, 4-[4-(Benzylaminomethyl)imidazol-1-ylmethyl]benzoate.

The invention also relates to pharmaceutical composition containing at least one compound of formula (I) (active ingredient) as defined above and one or several pharmaceutically acceptable excipients.

In one aspect the compounds may be administered by a variety of means including orally, parenterally, by inhalation spray, topically, vaginally or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl-p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringers solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In another aspect, the present invention is directed to the use of compounds of formula (I) for the use of these FBPase inhibitors as a method of treatment or prevention of diseases responsive to inhibition of gluconeogenesis and in diseases responsive to lowered blood glucose levels. The compounds are also useful in treating or preventing excess glycogen storage diseases and diseases such as cardiovascular diseases including atherosclerosis, myocardial ischemic injury, in treating or preventing type II diabetes mellitus and diseases such as metabolic disorders such as hypercholesterolemia, hyperlipidemia which are exacerbated by hyperinsulinema and hyperglycemia.

In a more general manner the invention relates to a method of treatment or prevention of any diseases caused or related to FBPase, by inducing in patients an inhibition of said FBPase.

For example if the compounds of the invention are administered orally as tablets or capsules, the dose could range from about 0.1 mg/kg/ to about 100 mg/kg, preferably from about 0.5 mg/kg to about 50 mg/kg, preferably from 1 mg/kg to 10 mg/kg, more preferably from about 2 mg/kg to about 5 mg/kg.

If consider that the patient weight could range from 10 kg to 100 kg and according to the above-mentioned doses the daily doses could be from about 1-10 mg/day to about 1,000-10,000 mg/day, preferably from about 5-50 mg/day to about 500-5,000 mg/day, preferably from about 10-100 mg/day to about 100-1,000 mg/day and more preferably from about 20-200 mg/day to about 50-500 mg/day.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a fructose 1,6-bisphosphatase inhibitor compound of formula (I) as defined hereinbefore.

The amount of active ingredient that may be combined with the carrier material to produce a single dosage form will vary depending upon several parameters as for example the host treated, the nature of the disease, the composition of the pharmaceutical preparation and the particular mode of administration.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The present invention also relates to manufacturing process of compounds of formula (I) as shown in FIG. 1 (Scheme 1: method A), FIG. 2 (Scheme 2: method B) and FIG. 3 (Scheme 3: method C), in which $R^2$ is either $R^{2a}$ or $R^{2b}$. The compounds useful according to the invention may be prepared, unless specifically specified, by the application or adaptation of known methods, by which are meant methods

METHOD A

Figure 1:
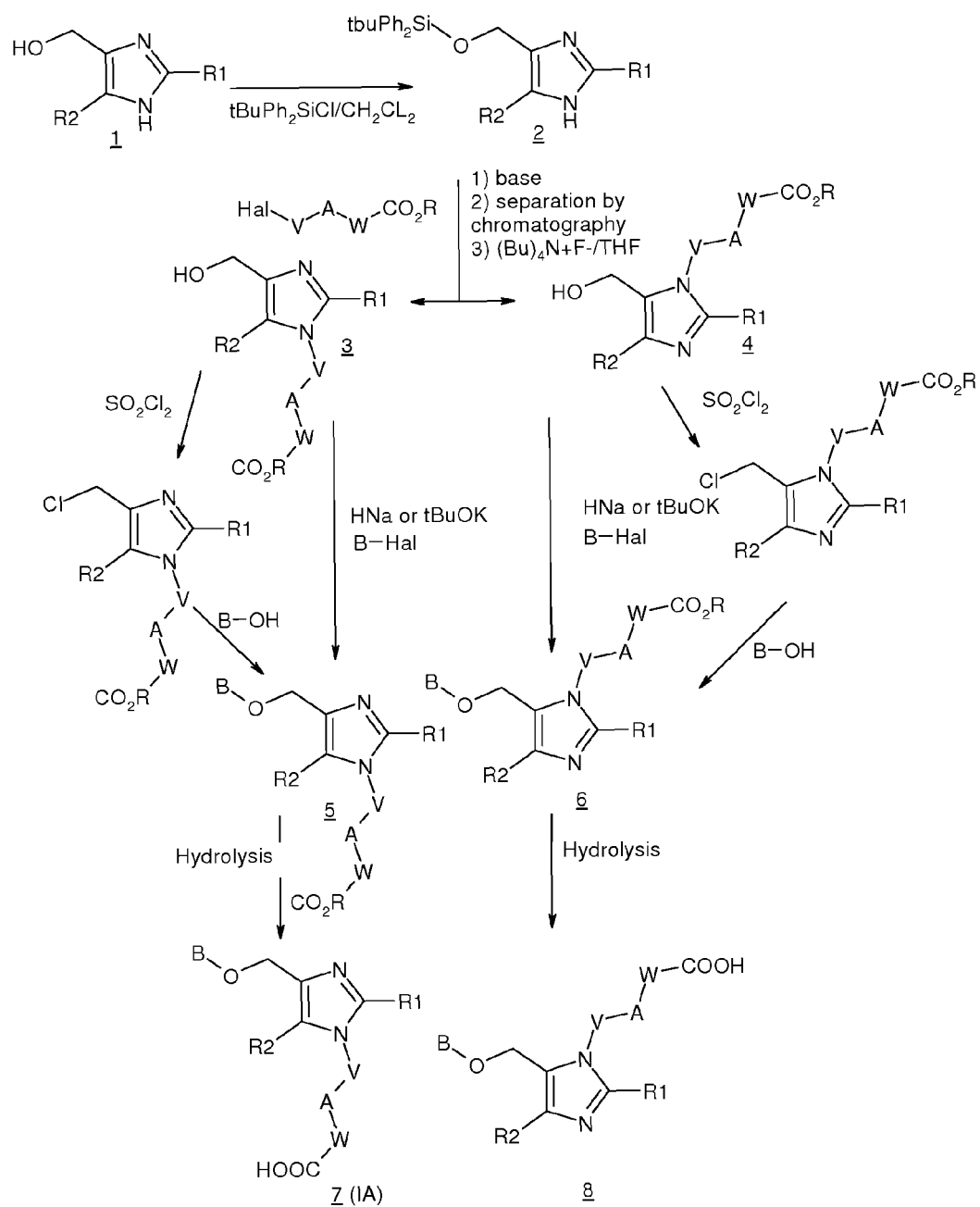
FIG. 1 illustrates a scheme for manufacturing compounds of formula (I)

Scheme 1, FIG. 1

This method is particularly suitable for compounds of formula (I) wherein $R^1=R^2=$hydrogen and $X=O$ (formula (IA)):

hydroxymethyl imidazoles 3 and 4 are prepared by condensation of protected hydroxymethylimidazoles 2 (see for example of protection *Chem. Pharm. Bull.* 37(6), 1481-1487, 1989) with halo esters in presence of base like triethylamine in an aprotic solvent followed by chromatographic separation of the two regioisomers and deprotection with tetrabutylammonium fluoride (see *protective groups in organic synthesis*, Greene, John Wiley & sons Ed 1991).

imidazoles 5 and 6 are obtained by condensation of compounds 3 or 4 according to Williamson et al. *J. Chem. Soc.*, (1852), 4, 229 with haloalkylarylcarboxylic esters in presence of a base like sodium alkoxyde, NaH or tBuOK, potassium carbonate, cesium carbonate in an inert solvent like dimethylformamide, toluene, THF, xylene, N-methylpyrrolidone, acetonitrile, at a temperature between 20° C. and the reflux of the solvent for 2 to 36 hours. Imidazoles 5 and 6 can also be prepared by treatment of the alcohols 3 and 4 with thionyl chloride to yield the corresponding chlorides followed by substitution with an alcohol, according to Williamson.

Imidazoles 7 (formula (IA) and 8 are obtained after hydrolysis without isolation of the esters 5 and 6.

In the context of the present specification, the term "hydrolysis" refers to the reaction of converting the ester group, for example as present in compounds 5 or 6, into the corresponding carboxylic group, for example as present in compounds 7 or 8 respectively.

Such reaction may be carried out according to any process known in the art, and for example under acidic or basic conditions (saponification).

As a particular variant, conversion of the ester groups to the carboxylic acid groups, for example of compounds 7 and 8, may occur while precursor compounds, for example compounds 3 and 4 respectively, are placed under basic conditions leading to compounds, in this case 5 and 6 respectively, which are consequently not isolated.

METHOD B

Figure 2:
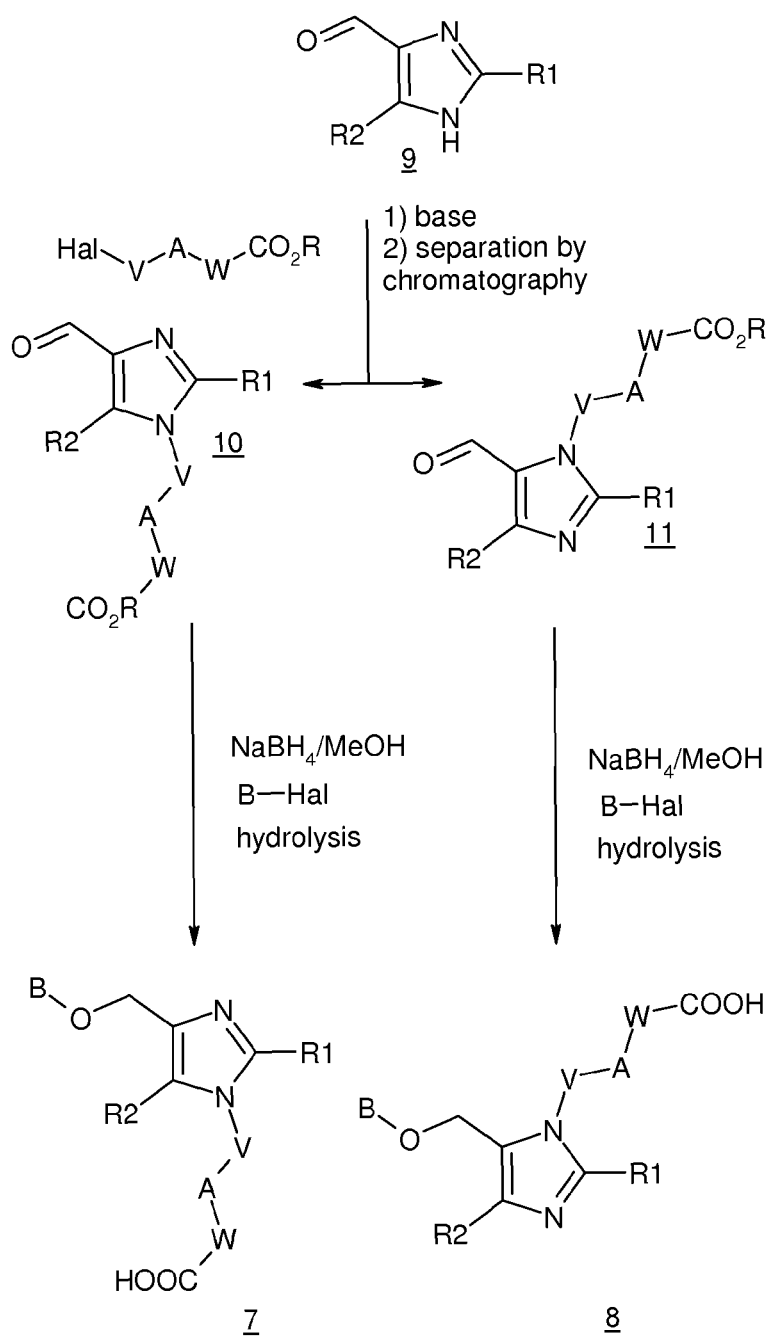
FIG. 2 illustrates another scheme for manufacturing compounds of formula (I)

Scheme 2, FIG. 2

This method is particularly suitable for compounds of formula (IA) wherein $R^1$ and/or $R^2$ are not hydrogen.

4-Formylimidazoles 9 are prepared according to Watson S P et al., *Synth. Commun.*, (1992), 22, 2971 by condensing alkyl imidates with 1,3-dihydroxyacetone.

Imidazoles esters 10 and 11 are then prepared by reaction of compound 9 with haloalkylarylcarboxylic esters in condition similar to method A. The two isomers 10 and 11 are separated by chromatography.

Imidazoles 7 and 8 are then obtained by reduction of compounds 10 and 11 with reductive agents like sodium borohydride in solvent like methanol, followed by etherification with B-Hal, where B is as defined above and Hal represents halogen, and finally hydrolysis, where the term "hydrolysis" is as defined above.

METHOD C

Figure 3:
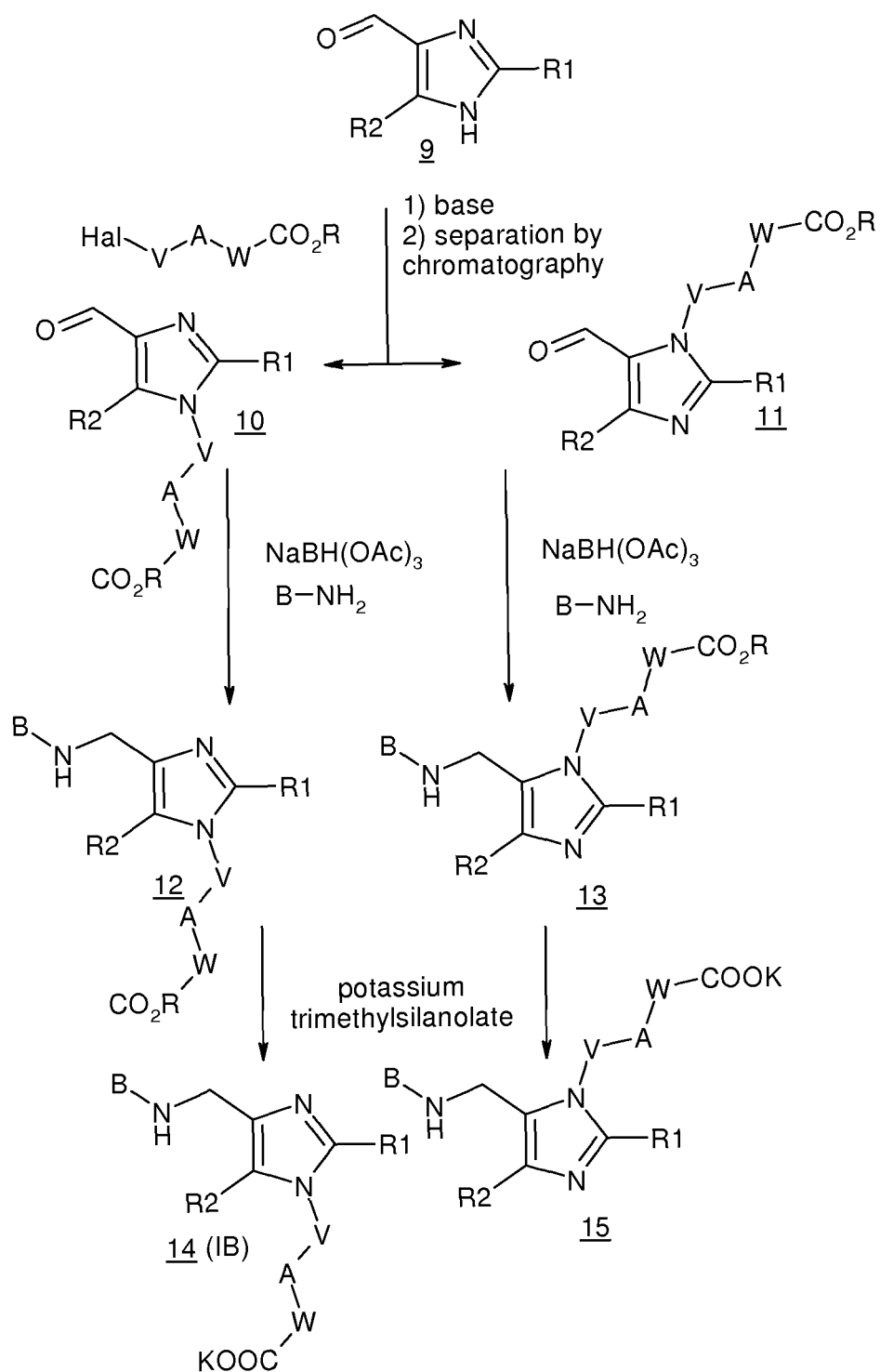
FIG. 3 illustrates a further scheme for manufacturing compounds of formula (I).

Scheme 3, FIG. 3

This method is particularly suitable for compounds of formula (I) wherein $X=$—NH— (formula (IB))

Imidazoles 12 and 13 are prepared by reductive amination of compounds 10 and 11 (prepared according to method B) with a hydride reducing agent. A preferred reagent is sodium triacetoxyborohydride (see Abdel-Magid et al., *J. Org. Chem.*, (1996), 61, 3849-3862). The reaction is carried out in 1,2-dichloroethane, THF, $CH_2Cl_2$, or acetonitrile. The standard reaction conditions are as follows: a mixture of the carbonyl compound and the amine (0-5% molar excess) in the desired solvent is stirred with 1.3-1.6 equivalent of sodium triacetoxyborohydride at room temperature for 1 to 36 hours.

Hydrolysis with mild basic agent gives compound 14 (formula (IB)) and compound 15. One preferred reagent is potassium trimethylsilanolate. The reaction is carried out under anhydrous conditions at room temperature for 2 hours to one week and yields the amino acids 14 and 15 as potassium salts.

The invention is illustrated by the following representative and non-limiting examples.

A) Preparation of the intermediates

Example A1

4-(4-hydroxymethylimidazol-1-ylmethyl)benzoic acid methyl ester a)
4-(tert-Butyldiphenylsilyloxymethyl)-1H-imidazole 4-Hydroxymethylimidazole hydrochloride ACROS (5 g, 37.1 mmol) was suspended in $CH_2Cl_2$ (100 ml) and TEA (12.87 ml, 92.8 mmol) was added. The solution was cooled at 0° C. and tert-butyldiphenylsilylchloride (15.3 ml, 55.7 mmol) was added. The reaction mixture was stirred for 30 min at 0° C. and at room temperature for 3.5 h. Water was added, the organic extract was washed with water and brine, then died over $MgSO_4$. The solvent was removed under reduced pressure and the resulting oil was crystallized from diisopropylether to afford a white solid (8.17 g, m.p.=135° C.).

$^1$H-NMR (200 MHz $CDCl_3$) δ (ppm): 0.99 (s, 9H), 4.69 (s, 2H), 6.8 (s, 1H), 7.2-7.65 (m, 11H).

b) 4-(4-tert-Butyldiphenylsilyloxymethylimidazol-1-ylmethyl)benzoic acid methyl ester and 4-(5-tert-Butyldiphenylsilyloxymethylimidazol-1-ylmethyl)-benzoic acid methyl ester A mixture of 4-(tert-butyldiphenylsilyloxymethyl)-1H-imidazole (9.25 g, 27.4 mmol), methyl 4-bromomethylbenzoate (6.297 g, 27.4 mmol) and TEA (2.782 ml, 27.4 mmol) in toluene (250 ml) was refluxed for 1.5 h. Water (500 ml) was added, the mixture was extracted with AcOEt, the organic phase washed with brine and dried over $MgSO_4$. The solvent was removed under reduced pressure and the resulting oil was purified by flash chromatography on silica gel ($CH_2Cl_2$/MeOH: 100/0 to 98/2) to give:
4-(4-tert-Butyldiphenylsilyloxymethylimidazol-1-ylmethyl) benzoic acid methyl ester as white solid (1.67 g, mp 105° C.)
$^1$H-NMR (200 MHz, $DMSOd_6$) δ (ppm): 0.95 (s, 9H), 3.83 (s, 3H), 4.57 (s, 2H), 5.26 (s, 2H), 7.01 (s, 1H), 7.3-7.41 (m, 10H), 7.62-7.64 (m, 2H), 7.71 (s, 1H), 7.90-7.94 (m, 2H).
And
4-(5-tert-Butyldiphenylsilyloxymethylimidazol-1-ylmethyl) benzoic acid methyl ester as oil (1.14 g).
$^1$H-NMR (200 MHz, $DMSOd_6$) δ (ppm): 0.86 (s, 9H), 3.82 (s, 3H), 4.5 (s, 2H), 5.38 (s, 2H), 6.8 (s, 1H), 7.16 (d, 2H), 7.3-7.5 (m, 10H), 7.78 (s, 1H), 7.88 (d, 2H).

c) 4-(4-hydroxymethylimidazol-1-ylmethyl)benzoic acid methyl ester

A mixture of 4-(4-tert-Butyldiphenylsilyloxymethylimidazol-1-yl-methyl)benzoic acid methyl ester (1.6 g, 3.3 mmol) and tetrabutylammonium fluoride 1M in THF (3.3 ml, 3.3 mmol) in THF (10 ml) was stirred under argon at room temperature for 2 h. Water (15 ml) was added, the mixture was extracted with AcOEt, the organic phase washed with water, brine and dried over $MgSO_4$.
The solvent was removed under reduced pressure and the resulting oil was purified by flash chromatography on silica gel ($CH_2Cl_2$/MeOH: 100/0 to 90/10) to give a white solid (0.65 g, m.p.=128° C.).
M+H=247
$^1$H-NMR (200 MHz, $DMSOd_6$) δ (ppm): 3.83 (s, 3H), 4.3 (s, 2H), 5.24 (s, 2H), 7.01 (s, 1H), 7.36 (d, 2H), 7.68 (s, 1H), 7.98 (d, 2H).

Example A2

4-(5-hydroxymethylimidazol-1-ylmethyl)benzoic acid methyl ester

A mixture of 4-(5-tert-butyldiphenylsilyloxymethylimidazol-1-ylmethyl)benzoic acid methyl ester (0.74 g, 1.52 mmol) and tetrabutylammonium fluoride 1M in THF (1.52 ml, 1.52 mmol) in THF (10 ml) was stirred under argon at room temperature for 2 h. Water (15 ml) was added, the mixture was extracted with AcOEt, the organic phase washed with water, brine and dried over $MgSO_4$. The solvent was removed under reduced pressure and the resulting oil was purified by flash chromatography on silica gel ($CH_2Cl_2$/MeOH: 100/0 to 90/10) to give a white solid (0.22 g, m.p.=139-140° C.).
M+H=247
$^1$H-NMR (200 MHz, $DMSOd_6$) δ (ppm): 3.83 (s, 3H), 4.28 (s, 2H), 5.33 (s, 2H), 6.84 (s, 1H), 7.25 (d, 2H), 7.71 (s, 1H), 7.92 (d, 2H).
The following intermediates were obtained using the same procedure as in Example A1 but replacing 4-hydroxymethylimidazole hydrochloride with 4-hydroxymethyl-5-methylimidazole.

Example A3

4-(4-hydroxymethyl-5-methylimidazol-1-ylmethyl) benzoic acid methyl ester m.p.=148° C.
M+H=261

$^1$H-NMR (200 MHz, $DMSOd_6$) δ (ppm): 2 (s, 3H), 3.83 (s, 3H), 4.28 (s, 2H), 5.23 (s, 2H), 7.22 (d, 2H), 7.63 (s, 1H), 7.92 (d, 2H)

Example A4

4-(5-hydroxymethyl-4-methyl-imidazol-1-ylmethyl)-benzoic acid methyl ester m.p.=163° C.
M+H=261
$^1$H-NMR (200 Mhz, $DMSOd_6$) δ (ppm): 2.06 (s, 3H), 3.82 (s, 3H), 4.23 (s, 2H), 5.26 (s, 2H), 7.23 (d, 2H), 7.59 (s, 1H), 7.91 (d, 2H).
The following compounds were obtained using the same procedure as in Example A1 but replacing 4-bromomethylbenzoic acid methyl ester with 5-chloromethylfuran-2-carboxylic acid ethyl ester.

Example A5

5-(4-hydroxymethylimidazol-1-ylmethyl)furan-2-carboxylic acid ethyl ester

M+H=251
$^1$H-NMR (200 MHz, $DMSOd_6$) δ (ppm): 1.24 (t, 3H), 4.2-4.4 (m, 4H), 5.29 (s, 2H), 6.61 (dl, 1H), 6.99 (s, 1H), 7.25 (dl, 1H), 7.63 (s, 1H).

Example A6

5-(5-hydroxymethylimidazol-1-ylmethyl)furan-2-carboxylic acid ethyl ester

M+H=251
$^1$H-NMR (200 MHz, $DMSOd_6$) δ (ppm): 1.25 (t, 3H), 4.24 (q, 2H), 4.42 (s, 2H), 5.33 (s, 2H), 6.52 (d, 1H), 6.80 (s, 1H), 7.24 (d, 1H), 7.65 (s, 1H).
The following compounds were obtained using the same procedure as in Example A1 but replacing 4-hydroxymethylimidazole hydrochloride with 4-hydroxymethyl-5-methylimidazole and 4-bromomethylbenzoic acid methyl ester by 5-chloromethylfuran-2-carboxylic acid ethyl ester.

Example A7

5-(4-hydroxymethyl-5-methylimidazol-1-ylmethyl) furan-2-carboxylic acid ethyl ester M+H=265
$^1$H-NMR (200 MHz, $DMSOd_6$) δ (ppm): 1.25 (t, 3H), 2.15 (sl, 3H), 4.2-4.4 (m, 4H), 5.25 (sl, 2H), 6.54 (dl, 1H), 7.24 (dl, 1H), 7.57 (s, 1H).

Example A8

5-(5-hydroxymethyl-4-methylimidazol-1-ylmethyl) furan-2-carboxylic acid ethyl ester M+H=265
$^1$H-NMR (200 MHz, $DMSOd_6$) δ (ppm): 1.25 (t, 3H), 2.07 (sl, 3H), 4.25 (q, 2H), 4.37 (sl, 2H), 5.3 (sl, 2H), 6.52 (dl, 1H), 7.24 (d, 1H), 7.55 (sl, 1H).

Example A9

4-(4-Formylimidazol-1-ylmethyl)benzoic acid methyl ester and

4-(5-Formyl-imidazol-1-ylmethyl)-benzoic acid methyl ester

To a suspension of NaH 60% (37.65 g, 0.94 mol) in DMF (175 ml) was carefully added a solution of 1-H-imidazole-4-carboxaldehyde (75.36 g, 0.784 mol) in DMF (350 ml). The mixture was stirred at room temperature for 0.5 h, then a solution of 4-bromomethylbenzoic acid methyl ester (215.6 g, 0.94 mol) in DMF (475 ml) was added and the reaction was stirred overnight. The solvent was evaporated under vacuum, the residue taken in ethyl acetate and water. The organic phase was separated, washed with brine and dried over $MgSO_4$. The crude oil was purified several times by flash chromatography on silica gel using (toluene/ethyl acetate/$NH_4OH$: 60/40/1) as eluent to give quantitatively the desired products.

4-(4-Formylimidazol-1-ylmethyl)benzoic acid methyl ester $^1$H-NMR (200 MHz, $DMSOd_6$) δ (ppm): 3.83 (s, 3H), 5.39 (s, 2H), 7.42 (d, 2H), 7.95 (d, 2H), 8.02 (s, 1H), 8.14 (s, 1H), 9.70 (s, 1H).

4-(5-Formylimidazol-1-ylmethyl)benzoic acid methyl ester $^1$H-NMR (200 MHz, $DMSOd_6$) δ (ppm): 3.82 (s, 3H), 5.60 (s, 2H), 7.26 (d, 2H), 7.9 (d, 2H), 7.96 (s, 1H), 8.28 (s, 1H), 9.69 (s, 1H).

Example A10

4-[2-(5-Chlorothiophen-2-yl)-4-hydroxymethylimidazol-1-ylmethyl]benzoic acid methyl ester a) [2-(5-Chlorothiophen-2-yl)-3H-imidazol-4-yl]methanol A mixture of 5-chlorothiophene-2-carboximidic acid ethyl ester (38.7 g, 0.171 mol), 15.4 g of dihydroxyacetone (0.171 mol) and 102.18 g of gaseous ammonia (6.0 mol) in 500 ml of methanol was heated at 77° C. in a high-pressure reactor. After cooling and evaporation under vacuum, ammonium chloride was filtered and washed with methanol. The filtrate was concentrated under vacuum and yielded 35.1 g of crude product, which was used without further purification.

b) 4-[2-(5-Chlorothiophen-2-yl)-4-hydroxymethylimidazol-1-ylmethyl]-benzoic acid methyl ester To a solution of 18.8 g (0.875 mol) of compound of step a) in 300 ml of acetonitrile was added 34.24 g (0.105 mol) of cesium carbonate. The reaction mixture was stirred at room temperature for ten minutes and 24.07 g (0.105 mol) of 4-bromomethylbenzoic acid methyl ester was added. The resulting mixture was heated under reflux for 5 h and subsequently evaporated to dryness in vacuum. The crude residue was purified by flash chromatography on silica gel ($CH_2Cl_2$/MeOH: 95/05) using chloromethane/methanol: 95/05 as eluent and then crystallized from diethyl ether to give a white solid (12.5 g).

The following compound was obtained using the same procedure as in Example A10 but replacing 5-chlorothiophene-2-carboximidic acid ethyl ester with 4-bromobenzamidic acid ethyl ester:

Example A11

4-[2-(4-bromophenyl)-4-hydroxymethylimidazol-1-ylmethyl]benzoic acid methyl ester Using the previously described intermediated the following compounds were prepared:

Example 1

4-[5-(Biphenyl-4-ylmethoxymethyl)imidazol-1-ylmethyl]benzoic acid

To a solution of 4-(5-hydroxymethylimidazol-1-ylmethyl)benzoic acid methyl ester of Example A2 (0.11 g, 0.44 mmol) in THF (4 ml), DMF (1 ml) was added portionwise tBuOK (50 mg, 0.44 mmol). The reaction mixture was stirred at room temperature for 1.5 h, then 4-chloromethylbiphenyl (90 mg, 0.44 mmol) in THF (1 ml) was added and the reaction was stirred overnight. The solvent was removed under reduced pressure, then water (10 ml) was added and the mixture was extracted with AcOEt. The organic phase was dried over $MgSO_4$ and the resulting oil was purified by flash chromatography on silica gel ($CH_2Cl_2$/MeOH: 95/05) to give a yellow solid (20 mg).

M+H=399

$^1$H-NMR (200 MHz, $DMSOd_6$) δ (ppm): 4.28 (sl, 2H), 5.33 (s, 2H), 5.38 (s, 2H), 6.84 (s, 1H), 7.25-7.70 (m, 12H), 7.98 (d, 2H).

The following compounds were obtained using the same procedure as in Example 1.

Example 2

4-[5-(Biphenyl-4-ylmethoxymethyl)-4-methylimidazol-1-ylmethyl]benzoic acid

M−H=411

Example 3

4-[4-(Biphenyl-4-ylmethoxymethyl)imidazol-1-ylmethyl]benzoic acid

M+H=399

Example 4

4-[4-(Biphenyl-4-ylmethoxymethyl)-5-methylimidazol-1-ylmethyl]benzoic acid

M+H=413

Example 5

5-[4-(Biphenyl-4-ylmethoxymethyl)-5-methylimidazol-1-ylmethyl]furan-2-carboxylic acid

M+H=403

Example 6

5-[5-(Biphenyl-4-ylmethoxymethyl)-4-methylimidazol-1-ylmethyl]furan-2-carboxylic acid

M+H=401

Example 7

4-(4-Benzyloxymethylimidazol-1-ylmethyl)benzoic acid

To a solution of 4-(4-hydroxymethylimidazol-1-yl-methyl)benzoic acid methyl ester of Example A1 (0.4 g, 1.6 mmol) in THF/DMF (6/4) was added portionwise NaH 60% (162 mg, 4 mmol). The reaction mixture was stirred at room temperature for 1.5 h, then benzyl bromide (328 mg, 1.92 mmol) was added and the reaction was stirred overnight. The solvent was removed under reduced pressure, then water (10 ml) was added and the mixture was extracted with $CH_2Cl_2$. The aqueous phase was acidified with HCl 1 N to pH=4 and extracted with $CH_2Cl_2$. The latest organic phase was dried over $MgSO_4$ and concentrated under vacuum. The crude product was purified by flash chromatography on silica gel ($CH_2Cl_2$/MeOH: 95/05) to give a white solid (17 mg).
M+H=323
$^1$H-NMR (300 MHz, DMSOd$_6$) δ (ppm): 4.34 (s, 2H), 4.48 (s, 2H), 5.25 (s, 2H), 7.19 (s, 1H), 7.25-7.35 (m, 7H), 7.74 (s, 1H), 7.9 (d, 2H).

The following compounds were obtained using the same procedure as in Example 7

Example 8

4-[4-(4-Methylbenzyloxymethyl)imidazol-1-ylmethyl]benzoic acid

M+H=337

Example 9

4-[4-(4-tert-Butylbenzyloxymethyl)imidazol-1-ylmethyl]benzoic acid

M+H=379

Example 10

4-[4-(Naphthalen-2-ylmethoxymethyl)imidazol-1-ylmethyl]benzoic acid

M+H=373

Example 11

4-[4-(3-Fluorobenzyloxymethyl)imidazol-1-ylmethyl]benzoic acid

M+H=341

Example 12

4-[4-(3-Bromobenzyloxymethyl)imidazol-1-ylmethyl]benzoic acid

M+H=402

Example 13

4-[4-(3-Methoxybenzyloxymethyl)imidazol-1-ylmethyl]benzoic acid

M+H=353

Example 14

4-[4-(2,4-Difluorobenzyloxymethyl)imidazol-1-ylmethyl]benzoic acid

M+H=359

Example 15

4-[4-(2-Chloro-4-fluorobenzyloxymethyl)imidazol-1-ylmethyl]benzoic acid

M+H=375

Example 16

4-[4-(3,5-Dimethoxybenzyloxymethyl)imidazol-1-ylmethyl]benzoic acid

M+H=383

Example 17

4-[4-(3-Methylbenzyloxymethyl)imidazol-1-ylmethyl]benzoic acid

M+H=337

Example 18

4-[4-(3-Chlorobenzyloxymethyl)imidazol-1-ylmethyl]benzoic acid

M+H=357

Example 19

4-[4-(3-Trifluoromethylbenzyloxymethyl)imidazol-1-ylmethyl]benzoic acid

M+H=391

Example 20

4-[4-(Biphenyl-3-ylmethoxymethyl)-2-(5-chlorothiophen-2-yl)imidazol-1-ylmethyl]benzoic acid

M+H=515

Example 21

4-[2-(5-Chlorothiophen-2-yl)-4-(4-cyanobenzyloxymethyl)imidazol-1-ylmethyl]benzoic acid

M+H=464

Example 22

4-[2-(5-Chlorothiophen-2-yl)-4-(2,5-dichlorobenzyloxymethyl)imidazol-1-ylmethyl]benzoic acid

M+H=509

Example 23

4-[4-(4-Bromobenzyloxymethyl)-2-(5-chlorothiophen-2-yl)imidazol-1-ylmethyl]benzoic acid

M+H=519

Example 24

4-[4-(3-Chlorobenzyloxymethyl)-2-(5-chlorothiophen-2-yl)imidazol-1-ylmethyl]benzoic acid

M+H=473

Example 25

4-[2-(5-Chlorothiophen-2-yl)-4-(2-methylbenzyloxymethyl)imidazol-1-ylmethyl]benzoic acid

M+H=453

Example 26

4-{2-(5-Chlorothiophen-2-yl)-4-[7-(5-methyl-[1,2,4]-oxadiazol-3-yl)naphthalen-2-ylmethoxymethyl]imidazol-1-ylmethyl}benzoic acid

M+H=571

Example 27

4-{2-(5-Chlorothiophen-2-yl)-4-[2-(5-methyl-[1,2,4]-oxadiazol-3-yl)benzyloxymethyl]imidazol-1-ylmethyl}benzoic acid

M+H=521

Example 28

4-[2-(5-Chlorothiophen-2-yl)-4-(3-cyanobenzyloxymethyl)imidazol-1-ylmethyl]benzoic acid

M+H=464

Example 29

4-[2-(5-Chlorothiophen-2-yl)-4-(2,6-difluorobenzyloxymethyl)imidazol-1-ylmethyl]benzoic acid

M+H=475

Example 30

4-[4-(2-Chlorobenzyloxymethyl)-2-(5-chlorothiophen-2-yl)imidazol-1-ylmethyl]benzoic acid

M+H=473

Example 31

4-[2-(5-Chlorothiophen-2-yl)-4-(2-fluorobenzyloxymethyl)imidazol-1-ylmethyl]benzoic acid

M+H=457

Example 32

4-[4-(4-Chlorobenzyloxymethyl)-2-(5-chlorothiophen-2-yl)imidazol-1-ylmethyl]benzoic acid

M+H=473

Example 33

4-[4-Benzyloxymethyl-2-(5-chlorothiophen-2-yl)imidazol-1-ylmethyl]benzoic acid

M+H=439

Example 34

4-[2-(5-Chlorothiophen-2-yl)-4-(3-methylbenzyloxymethyl)imidazol-1-ylmethyl]benzoic acid

M+H=453

Example 35

4-[2-(5-Chlorothiophen-2-yl)-4-(4-fluorobenzyloxymethyl)imidazol-1-ylmethyl]benzoic acid

M+H=457

Example 36

4-[2-(5-Chlorothiophen-2-yl)-4-(3-trifluoromethylbenzyloxymethyl)imidazol-1-ylmethyl]benzoic acid

M+H=507

Example 37

4-[2-(5-Chlorothiophen-2-yl)-4-(4-chloro-2-trifluoromethylquinolin-6-ylmethoxymethyl)imidazol-1-ylmethyl]benzoic acid

M+H=592

Example 38

4-[2-(5-Chlorothiophen-2-yl)-4-(2-cyanobenzyloxymethyl)imidazol-1-ylmethyl]benzoic acid

M+H=464

Example 39

4-[2-(5-Chlorothiophen-2-yl)-4-(naphthalen-2-ylmethoxymethyl)imidazol-1-ylmethyl]benzoic acid

M+H=489

Example 40

4-[2-(5-Chlorothiophen-2-yl)-4-(2-trifluoromethyl-benzyloxymethyl)imidazol-1-ylmethyl]benzoic acid

M+H=507

Example 41

4-[2-(5-Chlorothiophen-2-yl)-4-(4-methylbenzy-loxymethyl)imidazol-1-ylmethyl]benzoic acid

M+H=453

Example 42

4-[2-(4-Bromophenyl)-4-(2,5-dichlorobenzyloxym-ethyl)imidazol-1-ylmethyl]benzoic acid

M+H=547

Example 43

4-[4-(4-Bromobenzyloxymethyl)-2-(4-bromophenyl)imidazol-1-ylmethyl]benzoic acid

M+H=557

Example 44

4-[2-(4-Bromophenyl)-4-(3-chlorobenzyloxymethyl)imidazol-1-ylmethyl]benzoic acid

M+H=513

Example 45

4-{2-(4-Bromophenyl)-4-[2-(5-methyl-[1,2,4]-oxa-diazol-3-yl)benzyloxy-methyl]imidazol-1-ylmethyl}benzoic acid

M+H=559

Example 46

4-[2-(4-Bromophenyl)-4-(2-cyanobenzyloxymethyl)imidazol-1-ylmethyl]benzoic acid

M+H=504

Example 47

4-[2-(4-Bromophenyl)-4-(4-chlorobenzyloxymethyl)imidazol-1-ylmethyl]benzoic acid

M+H=512

Example 48

4-[2-(4-Bromophenyl)-4-(3-methylbenzyloxym-ethyl)imidazol-1-ylmethyl]benzoic acid

M+H=491

Example 49

4-[2-(4-Bromophenyl)-4-(4-fluorobenzyloxymethyl)imidazol-1-ylmethyl]benzoic acid

M+H=495

Example 50

4-[4-(Biphenyl-3-ylmethoxymethyl)-2-(4-bromophe-nyl)-imidazol-1-ylmethyl]benzoic acid

M+H=553

Example 51

4-[2-(4-Bromophenyl)-4-(4-cyanobenzyloxymethyl)imidazol-1-ylmethyl]benzoic acid

M+H=502

Example 52

4-[2-(4-Bromophenyl)-4-(naphthalen-2-yl-methoxymethyl)imidazol-1-ylmethyl]benzoic acid

M+H=529

Example 53

4-[2-(4-Bromophenyl)-4-(3-cyanobenzyloxymethyl)imidazol-1-ylmethyl]benzoic acid

M+H=504

Example 54

4-[2-(4-Bromophenyl)-4-(2-fluorobenzyloxymethyl)imidazol-1-ylmethyl]benzoic acid

M+H=495

Example 55

Potassium, 4-{4-[(4-fluorobenzylamino)methyl]imi-dazol-1-ylmethyl}benzoate

A mixture of 4-(4-formylimidazol-1-ylmethyl)benzoic acid methyl ester of Example A9 (400 mg, 1.64 mmol) and 4-fluorobenzylamine (205 mg, 1.64 mmol) in methylene chloride (5 ml) was stirred at room temperature for 15 minutes. Then triacetoxyborohydride (520 mg, 2.46 mmol) was added in one portion and the reaction was stirred overnight. The organic phase was washed by saturated solution of sodium hydrogenocarbonate, brine and dried over $MgSO_4$. After concentration under vacuum, the crude product was purified by chromatography on silica gel using $CH_2Cl_2$/MeOH/$NH_4OH$ (100/0/0-90/10/0-90/10/0.01) as eluent to afford a solid (267 mg).

Then a solution of the previous solid (256 mg), potassium trimethylsilanolate (273 mg, 1.2 eq) in methylene chloride (7.5 ml) was stirred at room temperature for 7 days. The precipitate was filtered, washed with methylene chloride, diethylether and dried under vacuum to give a brown solid (200 mg).

M+2H+=340.4

$^1$H-NMR (300 MHz, D$_2$O) δ (ppm): 3.42 (s, 2H), 3.45 (s, 2H), 4.99 (s, 2H), 6.76 (s, 1H), 6.8-7.1 (m, 6H), 7.51 (s, 1H), 7.61 (d, 2H).

The following compounds were obtained using the same procedure as in Example 55

Example 56

Potassium, 4-{4-[(3-methoxybenzylamino)methyl] imidazol-1-ylmethyl}benzoate

M+2H+=352.4

Example 57

Potassium, 4-{4-[(4-methoxybenzylamino)methyl] imidazol-1-ylmethyl}benzoate

M+2H+=352.4

Example 58

Potassium, 4-{4-[(3-trifluoromethylbenzylamino) methyl]imidazol-1-ylmethyl}benzoate

M+2H+=390.4

Example 59

Potassium, 4-{4-[(2-fluoro-4-bromobenzylamino) methyl]imidazol-1-ylmethyl}benzoate

M+2H+=418.1

Example 60

Potassium, 4-(4-{[(furan-2-ylmethyl)amino] methyl}imidazol-1-ylmethyl)benzoate

[M]$^-$=310.2

Example 61

Potassium, 4-(4-{[(pyridin-2-ylmethyl)amino] methyl}imidazol-1-ylmethyl)benzoate

[M]$^-$=321.2

Example 62

Potassium, 4-(4-{[(pyridin-4-ylmethyl)amino] methyl}imidazol-1-ylmethyl)benzoate

[M]$^-$=321.2

Example 63

Potassium, 4-[4-(benzylaminomethyl)imidazol-1-ylmethyl]benzoate

[M]$^-$=320.3

Biological Examples

Assays: Measurement of Inhibition Constants

Enzymatic activity was measured spectrophotometrically in reactions that coupled the formation of product (fructose 6-Phosphate) to the reduction of NADP+, using phosphoglucoisomerase (PGI) and glucose 6-phosphate dehydrogenase (G6PDH) as the coupling enzymes.

Reaction mixtures (250 μl) were made up in 96-well microtitre plates, and consisted of 20 mM triethanolamine, pH 7.5, 2 mM MgCl$_2$, 0.1 mM EDTA, 40 mM ammonium sulfate, 0.5 mM NADP, 1 U/ml G6PDH, 1 U/ml PGI and 0.167 mM substrate (Fructose 1,6-bisphosphate). The inhibitors were prepared at 10-2 M in DMSO 100% and tested at 10-5 M (DMSO 0.1%).

Reactions were started by the addition of the human liver recombinant Fructose-1,6-bisphosphatase and were monitored for 30 minutes at 340 nm in a Tecan Plate Reader (Room temperature). The IC$_{50}$ for AMP is around 10 μM and for Fructose-2,6-Bisphosphate around 35 μM.

Cellular Assays

Effects of the compounds previously described on hepatic glucose production in primary culture of rat hepatocytes.

Hepatocytes were isolated from normal Wistar rats in overnight fasted condition by collagenase perfusion as described by Seglen (*Methods Cell Biol.,* (1975); 13, 29-83). Cell viability was assessed by the trypan blue exclusion test. The isolated hepatocytes were suspended in William's medium containing 10% fetal bovine serum in 6 well plates. After cell attachment (4 h) the medium was changed to remove cellular debris and replaced by serum-free minimum essential medium without glucose and the hepatocytes were cultured for 16-18 h (37° C.; 5%, CO$_2$). At the end of the culture and after removing the medium, glucose production was assessed by incubating hepatocytes for 3 h in KREBS buffer supplemented with dihydroxyacetone (DHA) as a gluconeogenic precursor in the presence or not of the different compounds previously described. After the 3 h incubation time, the amount of glucose in the buffer was assayed by a glucose oxidase method (GOD). The total amount of cellular protein per well was measured by the method of Lowry. The results were expressed as nanomoles of glucose produced per mg cell protein. The activity of the tested compounds was expressed as % of control glucose production in presence of DHA and without compound (100%).

| Ex n° | Inhibition of human F-1,6-Bpase IC$_{50}$ (μM) | Hepatic glucose production (rat hepatocytes) % of control at 100 μM |
|---|---|---|
| 20 | 70.2 | 10 |
| 26 | 51.2 | 44 |
| 47 | 88.3 | 61 |

The invention claimed is:

1. An imidazole compound of formula (I):

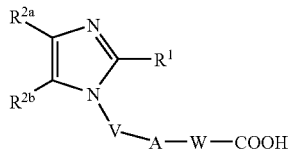

wherein:
R$^1$ is selected from the group consisting of hydrogen, (C$_1$-C$_6$)alkyl, (C$_3$-C$_{10}$)cycloalkyl, aryl, heteroaryl, heterocycloalkyl, aralkyl and heteroaralkyl;
R$^{2a}$ and R$^{2b}$ are
either R$^{2a}$ represents —CH$_2$—X—Z—B and R$^{2b}$ is selected from the group consisting of hydrogen and (C$_1$-C$_6$)alkyl;
or R$^{2a}$ is selected from the group consisting of hydrogen and (C$_1$-C$_6$)alkyl and R$^{2b}$ represents —CH$_2$—X—Z—B;
A is a divalent radical selected from the group consisting of aryl, heteroaryl, aralkyl and heteroaralkyl;
B is selected from the group consisting of aryl, heteroaryl, aralkyl and heteroaralkyl;
V and W, independently from one another, each represent a single bond or are selected from the group consisting of alkylene, alkyleneoxyalkylene, alkenylene and alkynylene;
X is selected from the group consisting of —NR—, —O—, —S—, —SO— and —SO$_2$—, with R being hydrogen or an unsubstituted (C$_1$-C$_6$)alkyl;
Z represents —(CH$_2$)$_m$—, with m being 1, 2, 3, 4, 5 or 6;
or a stereoisomer or diastereoisomer thereof, or a mixture thereof, a racemic mixture thereof, or an oxide, prodrug or pharmaceutically acceptable salt thereof.

2. An imidazole compound of claim 1 wherein:
R$^1$ is selected from the group consisting of hydrogen, aryl and heteroaryl;
R$^{2a}$ represents —CH$_2$—X—Z—B and R$^{2b}$ represents hydrogen or lower alkyl; or
R$^{2b}$ represents —CH$_2$—X—Z—B and R$^{2a}$ represents hydrogen or lower alkyl;
A represents a bivalent radical (A$^1$) or (A$^2$):

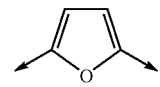

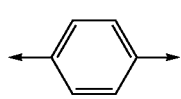

B is selected from the group consisting of aryl, heteroaryl, aralkyl and heteroaralkyl;
V represents —CH$_2$—;
W represents a single bond;
X represents —O—; and
Z represents —CH$_2$—,
or a stereoisomer or diastereoisomer thereof, or a mixture thereof, a racemic mixture thereof, or an oxide, prodrug or pharmaceutically acceptable salt thereof.

3. An imidazole compound of claim 1 wherein:
R$^1$ is selected from the group consisting of hydrogen, aryl and heteroaryl;
R$^{2a}$ represents —CH$_2$—X—Z—B and R$^{2b}$ represents hydrogen or lower alkyl; or
R$^{2b}$ represents —CH$_2$—X—Z—B and R$^{2a}$ represents hydrogen or lower alkyl;
B is selected from the group consisting of the following B$^1$-B$^5$ radicals:

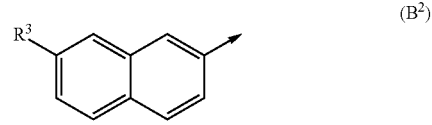

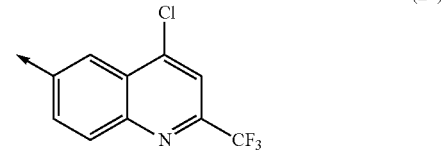

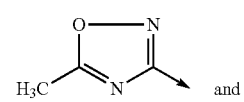

and

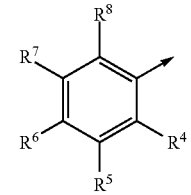

where each of R$^3$ to R$^8$ are independently selected from the group consisting of lower alkyl, lower aryl, lower aralkyl, lower cycloalkyl and heterocycloalkyl, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, carbonylamino, carboxamido, nitro, acyloxy, aminoalkyl, alkylaminoaryl, alkylaryl, alkylaminoalkyl, alkoxyaryl, arylamino, aralkylamino, phosphono, sulfonyl, carboxamidoalkylaryl, carboxamidoaryl, hydroxyalkyl, halo, haloalkyl, alkylaminoalkylcarbonyl, aminocarboxamidoalkyl, cyano, lower alkoxyalkyl, lower perhaloalkyl, perhaloalkoxy, and arylalkyloxyalkyl,
A represents a bivalent radical (A$^1$) or (A$^2$):

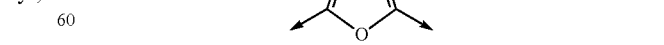

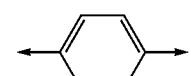

V represents —CH$_2$—;
W represents a single bond;
X represents —O—; and
Z represents —CH$_2$—, or a stereoisomer or diastereoisomer thereof, or a mixture thereof, a racemic mixture thereof, or an oxide, prodrug or pharmaceutically acceptable salt thereof.

4. An imidazole compound of claim 1 wherein:

R$^1$ is selected from the group consisting of hydrogen, aryl and heteroaryl;

R$^{2a}$ represents —CH$_2$—X—Z—B and R$^{2b}$ represents hydrogen or lower alkyl; or R$^{2b}$ represents —CH$_2$—X—Z—B and R$^{2a}$ represents hydrogen or lower alkyl;

B is selected from the group consisting of the following B$^1$-B$^5$ radicals:

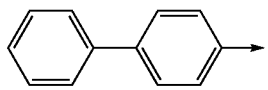 (B$^1$)

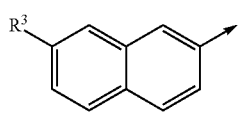 (B$^2$)

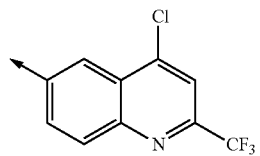 (B$^3$)

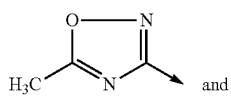 (B$^4$)

and

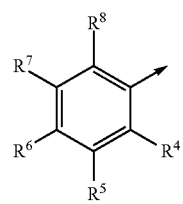 (B$^5$)

wherein

R$^3$ represents the following radical:

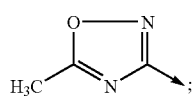

R$^4$, R$^5$, R$^6$, R$^7$ and R$^8$ are each independently from one another selected from the group consisting of hydrogen, Cl, Br, F, CF$_3$, CN, CH$_3$, CH$_3$O, tert-butyl and the radical of formula:

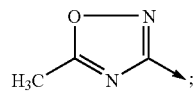

A represents a bivalent radical (A$^1$) or (A$^2$):

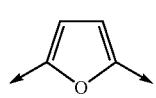 (A$^1$)

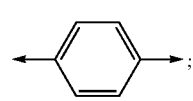 (A$^2$)

V represents —CH$_2$—;
W represents a single bond;
X represents —O—; and
Z represents —CH$_2$—, or a stereoisomer or diastereoisomer thereof, or a mixture thereof, a racemic mixture thereof, or an oxide, prodrug or pharmaceutically acceptable salt thereof.

5. An imidazole compound of claim 1 wherein:

R$^1$ is selected from the group consisting of hydrogen, and radical R$^{1a}$ and R$^{1b}$:

 (R$^{1a}$)

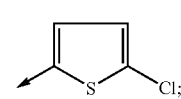 (R$^{1b}$)

R$^{2a}$ represents —CH$_2$—X—Z—B and R$^{2b}$ represents hydrogen or lower alkyl; or R$^{2b}$ represents —CH$_2$—X—Z—B and R$^{2a}$ represents hydrogen or lower alkyl;

B is selected from the group consisting of the following B$^1$-B$^5$ radicals:

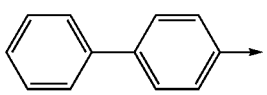 (B$^1$)

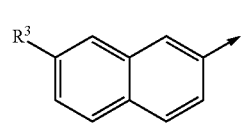 (B$^2$)

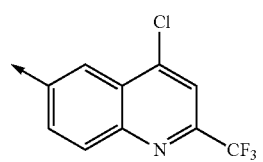 (B$^3$)

-continued

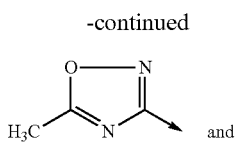 (B⁴)

and

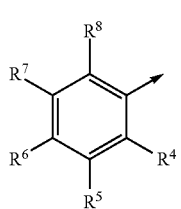 (B⁵)

wherein:
R³ represents the following radical:

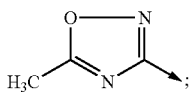

R⁴, R⁵, R⁶, R⁷ and R⁸ are each independently from one another selected from the group consisting of hydrogen, Cl, Br, F, CF₃, CN, CH₃, CH₃O, tert-butyl and the radical of formula:

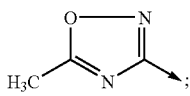

A represents a bivalent radical (A¹) or (A²):

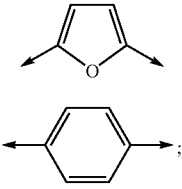

V represents —CH₂—;
W represents a single bond;
X represents —O—; and
Z represents —CH₂—,
or a stereoisomer or diastereoisomer thereof, or a mixture thereof, a racemic mixture thereof, or an oxide, prodrug or pharmaceutically acceptable salt thereof.

6. An imidazole compound of claim 1, which is selected from the group consisting of:
  4-[5-(Biphenyl-4-ylmethoxymethyl)imidazol-1-ylmethyl]benzoic acid;
  4-[5-(Biphenyl-4-ylmethoxymethyl)-4-methylimidazol-1-ylmethyl]benzoic acid;
  4-[4-(Biphenyl-4-ylmethoxymethyl)imidazol-1-ylmethyl]benzoic acid;
  4-[4-(Biphenyl-4-ylmethoxymethyl)-5-methylimidazol-1-ylmethyl]benzoic acid;
  5-[4-(Biphenyl-4-ylmethoxymethyl)-5-methylimidazol-1-ylmethyl]-furan-2-carboxylic acid;
  5-[5-(Biphenyl-4-ylmethoxymethyl)-4-methylimidazol-1-ylmethyl]furan-2-carboxylic acid;
  4-(4-Benzyloxymethylimidazol-1-ylmethyl)benzoic acid;
  4-[4-(4-Methylbenzyloxymethyl)imidazol-1-ylmethyl]benzoic acid;
  4-[4-(4-tert-Butylbenzyloxymethyl)imidazol-1-ylmethyl]benzoic acid;
  4-[4-(Naphthalen-2-ylmethoxymethyl)imidazol-1-ylmethyl]benzoic acid;
  4-[4-(3-Fluorobenzyloxymethyl)imidazol-1-ylmethyl]benzoic acid;
  4-[4-(3-Bromobenzyloxymethyl)imidazol-1-ylmethyl]benzoic acid;
  4-[4-(3-Methoxybenzyloxymethyl)imidazol-1-ylmethyl]benzoic acid;
  4-[4-(2,4-Difluorobenzyloxymethyl)imidazol-1-ylmethyl]benzoic acid;
  4-[4-(2-Chloro-4-fluorobenzyloxymethyl)imidazol-1-ylmethyl]benzoic acid;
  4-[4-(3,5-Dimethoxybenzyloxymethyl)imidazol-1-ylmethyl]benzoic acid;
  4-[4-(3-Methylbenzyloxymethyl)imidazol-1-ylmethyl]benzoic acid;
  4-[4-(3-Chlorobenzyloxymethyl)imidazol-1-ylmethyl]benzoic acid;
  4-[4-(3-Trifluoromethylbenzyloxymethyl)imidazol-1-ylmethyl]benzoic acid;
  4-[4-(Biphenyl-3-ylmethoxymethyl)-2-(5-chlorothiophen-2-yl)imidazol-1-ylmethyl]benzoic acid;
  4-[2-(5-Chlorothiophen-2-yl)-4-(4-cyanobenzyloxymethyl)imidazol-1-ylmethyl]benzoic acid;
  4-[2-(5-Chlorothiophen-2-yl)-4-(2,5-dichlorobenzyloxymethyl)imidazol-1-ylmethyl]benzoic acid;
  4-[4-(4-Bromobenzyloxymethyl)-2-(5-chlorothiophen-2-yl)imidazol-1-ylmethyl]benzoic acid;
  4-[4-(3-Chlorobenzyloxymethyl)-2-(5-chlorothiophen-2-yl)imidazol-1-ylmethyl]benzoic acid;
  4-[2-(5-Chlorothiophen-2-yl)-4-(2-methylbenzyloxymethyl)imidazol-1-ylmethyl]benzoic acid;
  4-{2-(5-Chlorothiophen-2-yl)-4-[7-(5-methyl-[1,2,4]oxadiazol-3-yl)-naphthalen-2-ylmethoxymethyl]imidazol-1-ylmethyl}benzoic acid;
  4-{2-(5-Chlorothiophen-2-yl)-4-[2-(5-methyl-[1,2,4]oxadiazol-3-yl)benzyloxymethyl]imidazol-1-ylmethyl}benzoic acid;
  4-[2-(5-Chlorothiophen-2-yl)-4-(3-cyanobenzyloxymethyl)imidazol-1-ylmethyl]benzoic acid;
  4-[2-(5-Chlorothiophen-2-yl)-4-(2,6-difluorobenzyloxymethyl)imidazol-1-ylmethyl]benzoic acid;
  4-[4-(2-Chlorobenzyloxymethyl)-2-(5-chlorothiophen-2-yl)imidazol-1-ylmethyl]benzoic acid;
  4-[2-(5-Chlorothiophen-2-yl)-4-(2-fluorobenzyloxymethyl)imidazol-1-ylmethyl]benzoic acid;
  4-[4-(4-Chlorobenzyloxymethyl)-2-(5-chlorothiophen-2-yl)imidazol-1-ylmethyl]benzoic acid;
  4-[4-Benzyloxymethyl-2-(5-chlorothiophen-2-yl)imidazol-1-ylmethyl]benzoic acid;
  4-[2-(5-Chlorothiophen-2-yl)-4-(3-methylbenzyloxymethyl)imidazol-1-ylmethyl]benzoic acid;
  4-[2-(5-Chlorothiophen-2-yl)-4-(4-fluorobenzyloxymethyl)imidazol-1-ylmethyl]benzoic acid;
  4-[2-(5-Chlorothiophen-2-yl)-4-(3-trifluoromethylbenzyloxymethyl)imidazol-1-ylmethyl]benzoic acid;
  4-[2-(5-Chlorothiophen-2-yl)-4-(4-chloro-2-trifluoromethylquinolin-6-ylmethoxymethyl)imidazol-1-ylmethyl]benzoic acid;

4-[2-(5-Chlorothiophen-2-yl)-4-(2-cyanobenzyloxymethyl)imidazol-1-ylmethyl]benzoic acid;
4-[2-(5-Chlorothiophen-2-yl)-4-(naphthalen-2-ylmethoxymethyl)imidazol-1-ylmethyl]benzoic acid;
4-[2-(5-Chlorothiophen-2-yl)-4-(2-trifluoromethylbenzyloxymethyl)imidazol-1-ylmethyl]benzoic acid;
4-[2-(5-Chlorothiophen-2-yl)-4-(4-methylbenzyloxymethyl)imidazol-1-ylmethyl]benzoic acid;
4-[2-(4-Bromophenyl)-4-(2,5-dichlorobenzyloxymethyl)imidazol-1-ylmethyl]benzoic acid;
4-[4-(4-Bromobenzyloxymethyl)-2-(4-bromophenyl)-imidazol-1-ylmethyl]benzoic acid;
4-[2-(4-Bromophenyl)-4-(3-chlorobenzyloxymethyl)imidazol-1-ylmethyl]benzoic acid;
4-{2-(4-Bromophenyl)-4-[2-(5-methyl-[1,2,4]-oxadiazol-3-yl)benzyloxymethyl]imidazol-1-ylmethyl}benzoic acid;
4-[2-(4-Bromophenyl)-4-(2-cyanobenzyloxymethyl)imidazol-1-ylmethyl]benzoic acid;
4-[2-(4-Bromophenyl)-4-(4-chlorobenzyloxymethyl)imidazol-1-ylmethyl]benzoic acid;
4-[2-(4-Bromophenyl)-4-(3-methylbenzyloxymethyl)imidazol-1-ylmethyl]benzoic acid;
4-[2-(4-Bromophenyl)-4-(4-fluorobenzyloxymethyl)imidazol-1-ylmethyl]benzoic acid;
4-[4-(Biphenyl-3-ylmethoxymethyl)-2-(4-bromophenyl)imidazol-1-ylmethyl]benzoic acid;
4-[2-(4-Bromophenyl)-4-(4-cyanobenzyloxymethyl)imidazol-1-ylmethyl]benzoic acid;
4-[2-(4-Bromophenyl)-4-(naphthalen-2-ylmethoxymethyl)imidazol-1-ylmethyl]benzoic acid;
4-[2-(4-Bromophenyl)-4-(3-cyanobenzyloxymethyl)imidazol-1-ylmethyl]benzoic acid; and
4-[2-(4-Bromophenyl)-4-(2-fluorobenzyloxymethyl)imidazol-1-ylmethyl]benzoic acid,
or a stereoisomer or diastereoisomer thereof, or a mixture thereof, a racemic mixture thereof, or an oxide, prodrug or pharmaceutically acceptable salt thereof.

7. A potassium salt of an imidazole compound of claim 1 wherein:
$R^1$ represents hydrogen;
$R^{2a}$ represents —CH$_2$—X—Z—B and $R^{2b}$ represents hydrogen; or
$R^{2b}$ represents —CH$_2$—X—Z—B and $R^{2a}$ represents hydrogen;
A represents:

B is selected from the group consisting of

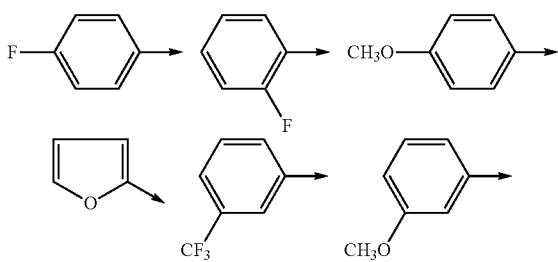

-continued

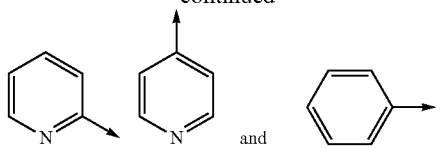

V represents —CH$_2$—;
W represents a single bond;
X represents —NH—; and
Z represents —CH$_2$—,
or a stereoisomer or diastereoisomer thereof, or a mixture thereof, a racemic mixture thereof, or an oxide or prodrug thereof.

8. A potassium salt according to claim 7, which is selected from the group consisting of:
Potassium, 4-{4-[(4-fluorobenzylamino)methyl]imidazol-1-ylmethyl}benzoate;
Potassium, 4-{4-[(3-methoxybenzylamino)methyl]imidazol-1-ylmethyl}benzoate;
Potassium, 4-{4-[(4-methoxybenzylamino)methyl]imidazol-1-ylmethyl}benzoate;
Potassium, 4-{4-[(3-trifluoromethylbenzylamino)methyl]imidazol-1-ylmethyl}benzoate;
Potassium, 4-{4-[(2-fluoro-4-bromobenzylamino)methyl]imidazol-1-ylmethyl}benzoate;
Potassium, 4-(4-{[(Furan-2-ylmethyl)amino]methyl}imidazol-1-ylmethyl)benzoate;
Potassium, 4-(4-{[(Pyridin-2-ylmethyl)amino]methyl}imidazol-1-ylmethyl)benzoate;
Potassium, 4-(4-{[(Pyridin-4-ylmethyl)amino]methyl}imidazol-1-ylmethyl)benzoate; and
Potassium, 4-[4-(Benzylaminomethyl)imidazol-1-ylmethyl]benzoate,
or a stereoisomer or diastereoisomer thereof, or a mixture thereof, a racemic mixture thereof, or an oxide, or prodrug thereof.

9. A pharmaceutical composition comprising at least one compound of formula (I) as claimed in claim 1, and one or several pharmaceutically acceptable excipients.

10. A method for inhibition of FBPase or for the treatment of diseases responsive to inhibition of gluconeogenesis and to lowered glucose levels, comprising administering to a subject in need thereof an effective amount of a compound of claim 1 wherein said diseases are selected from atherosclerosis, myocardial ischemic injury, type II diabetes mellitus, hypercholesterolemia, hyperlipidemia which is exacerbated by hyperinsulinema and hyperglycemia.

11. An imidazole compound of claim 1, or a pharmaceutically acceptable salt thereof.

12. An imidazole compound of claim 2, or a pharmaceutically acceptable salt thereof.

13. An imidazole compound of claim 3, or a pharmaceutically acceptable salt thereof.

14. An imidazole compound of claim 1, which is selected from the group consisting of:
4-[5-(Biphenyl-4-ylmethoxymethyl)imidazol-1-ylmethyl]benzoic acid;
4-[5-(Biphenyl-4-ylmethoxymethyl)-4-methylimidazol-1-ylmethyl]benzoic acid;
4-[4-(Biphenyl-4-ylmethoxymethyl)imidazol-1-ylmethyl]benzoic acid;
4-[4-(Biphenyl-4-ylmethoxymethyl)-5-methylimidazol-1-ylmethyl]benzoic acid;
5-[4-(Biphenyl-4-ylmethoxymethyl)-5-methylimidazol-1-ylmethyl]-furan-2-carboxylic acid;

5-[5-(Biphenyl-4-ylmethoxymethyl)-4-methylimidazol-1-ylmethyl]-furan-2-carboxylic acid;
4-(4-Benzyloxymethylimidazol-1-ylmethyl)benzoic acid;
4-[4-(4-Methylbenzyloxymethyl)imidazol-1-ylmethyl] benzoic acid;
4-[4-(4-tert-Butylbenzyloxymethyl)imidazol-1-ylmethyl] benzoic acid;
4-[4-(Naphthalen-2-ylmethoxymethyl)imidazol-1-ylmethyl]benzoic acid;
4-[4-(3-Fluorobenzyloxymethyl)imidazol-1-ylmethyl] benzoic acid;
4-[4-(3-Bromobenzyloxymethyl)imidazol-1-ylmethyl] benzoic acid;
4-[4-(3-Methoxybenzyloxymethyl)imidazol-1-ylmethyl] benzoic acid;
4-[4-(2,4-Difluorobenzyloxymethyl)imidazol-1-ylmethyl]benzoic acid;
4-[4-(2-Chloro-4-fluorobenzyloxymethyl)imidazol-1-ylmethyl]benzoic acid;
4-[4-(3,5-Dimethoxybenzyloxymethyl)imidazol-1-ylmethyl]benzoic acid;
4-[4-(3-Methylbenzyloxymethyl)imidazol-1-ylmethyl] benzoic acid;
4-[4-(3-Chlorobenzyloxymethyl)imidazol-1-ylmethyl] benzoic acid;
4-[4-(3-Trifluoromethylbenzyloxymethyl)imidazol-1-ylmethyl]benzoic acid;
4-[4-(Biphenyl-3-ylmethoxymethyl)-2-(5-chlorothiophen-2-yl)imidazol-1-ylmethyl]benzoic acid;
4-[2-(5-Chlorothiophen-2-yl)-4-(4-cyanobenzyloxymethyl)imidazol-1-ylmethyl]benzoic acid;
4-[2-(5-Chlorothiophen-2-yl)-4-(2,5-dichlorobenzyloxymethyl)imidazol-1-ylmethyl]benzoic acid;
4-[4-(4-Bromobenzyloxymethyl)-2-(5-chlorothiophen-2-yl)imidazol-1-ylmethyl]benzoic acid;
4-[4-(3-Chlorobenzyloxymethyl)-2-(5-chlorothiophen-2-yl)imidazol-1-ylmethyl]benzoic acid;
4-[2-(5-Chlorothiophen-2-yl)-4-(2-methylbenzyloxymethyl)imidazol-1-ylmethyl]benzoic acid;
4-{2-(5-Chlorothiophen-2-yl)-4-[7-(5-methyl-[1,2,4]oxadiazol-3-yl)-naphthalen-2-ylmethoxymethyl]imidazol-1-ylmethyl}benzoic acid;
4-{2-(5-Chlorothiophen-2-yl)-4-[2-(5-methyl-[1,2,4]oxadiazol-3-yl)benzyloxymethyl]imidazol-1-ylmethyl}benzoic acid;
4-[2-(5-Chlorothiophen-2-yl)-4-(3-cyanobenzyloxymethyl)imidazol-1-ylmethyl]benzoic acid;
4-[2-(5-Chlorothiophen-2-yl)-4-(2,6-difluorobenzyloxymethyl)imidazol-1-ylmethyl]benzoic acid;
4-[4-(2-Chlorobenzyloxymethyl)-2-(5-chlorothiophen-2-yl)imidazol-1-ylmethyl]benzoic acid;
4-[2-(5-Chlorothiophen-2-yl)-4-(2-fluorobenzyloxymethyl)imidazol-1-ylmethyl]benzoic acid;
4-[4-(4-Chlorobenzyloxymethyl)-2-(5-chlorothiophen-2-yl)imidazol-1-ylmethyl]benzoic acid;
4-[4-Benzyloxymethyl-2-(5-chlorothiophen-2-yl)imidazol-1-ylmethyl]benzoic acid;
4-[2-(5-Chlorothiophen-2-yl)-4-(3-methylbenzyloxymethyl)imidazol-1-ylmethyl]benzoic acid;
4-[2-(5-Chlorothiophen-2-yl)-4-(4-fluorobenzyloxymethyl)imidazol-1-ylmethyl]benzoic acid;
4-[2-(5-Chlorothiophen-2-yl)-4-(3-trifluoromethylbenzyloxymethyl)imidazol-1-ylmethyl]benzoic acid;
4-[2-(5-Chlorothiophen-2-yl)-4-(4-chloro-2-trifluoromethylquinolin-6-ylmethoxymethyl)imidazol-1-ylmethyl]benzoic acid;
4-[2-(5-Chlorothiophen-2-yl)-4-(2-cyanobenzyloxymethyl)imidazol-1-ylmethyl]benzoic acid;
4-[2-(5-Chlorothiophen-2-yl)-4-(naphthalen-2-ylmethoxymethyl)imidazol-1-ylmethyl]benzoic acid;
4-[2-(5-Chlorothiophen-2-yl)-4-(2-trifluoromethylbenzyloxymethyl)imidazol-1-ylmethyl]benzoic acid;
4-[2-(5-Chlorothiophen-2-yl)-4-(4-methylbenzyloxymethyl)imidazol-1-ylmethyl]benzoic acid;
4-[2-(4-Bromophenyl)-4-(2,5-dichlorobenzyloxymethyl) imidazol-1-ylmethyl]benzoic acid;
4-[4-(4-Bromobenzyloxymethyl)-2-(4-bromophenyl)-imidazol-1-ylmethyl]benzoic acid;
4-[2-(4-Bromophenyl)-4-(3-chlorobenzyloxymethyl)imidazol-1-ylmethyl]benzoic acid;
4-{2-(4-Bromophenyl)-4-[2-(5-methyl-[1,2,4]-oxadiazol-3-yl)benzyloxymethyl]imidazol-1-ylmethyl}benzoic acid;
4-[2-(4-Bromophenyl)-4-(2-cyanobenzyloxymethyl)imidazol-1-ylmethyl]benzoic acid;
4-[2-(4-Bromophenyl)-4-(4-chlorobenzyloxymethyl)imidazol-1-ylmethyl]benzoic acid;
4-[2-(4-Bromophenyl)-4-(3-methylbenzyloxymethyl) imidazol-1-ylmethyl]benzoic acid;
4-[2-(4-Bromophenyl)-4-(4-fluorobenzyloxymethyl)imidazol-1-ylmethyl]benzoic acid;
4-[4-(Biphenyl-3-ylmethoxymethyl)-2-(4-bromophenyl) imidazol-1-ylmethyl]benzoic acid;
4-[2-(4-Bromophenyl)-4-(4-cyanobenzyloxymethyl)imidazol-1-ylmethyl]benzoic acid;
4-[2-(4-Bromophenyl)-4-(naphthalen-2-ylmethoxymethyl)imidazol-1-ylmethyl]benzoic acid;
4-[2-(4-Bromophenyl)-4-(3-cyanobenzyloxymethyl)imidazol-1-ylmethyl]benzoic acid; and
4-[2-(4-Bromophenyl)-4-(2-fluorobenzyloxymethyl)imidazol-1-ylmethyl]benzoic acid,
or a pharmaceutically acceptable salt thereof.

15. A potassium salt of an imidazole compound of claim 1 wherein:

$R^1$ represents hydrogen;

$R^{2a}$ represents —CH$_2$—X—Z—B and $R^{2b}$ hydrogen; or $R^{2b}$ represents —CH$_2$—X—Z—B and $R^{2a}$ represents hydrogen;

A represents:

B is selected from the group consisting of

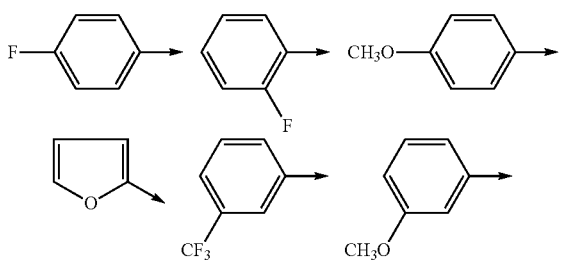

-continued

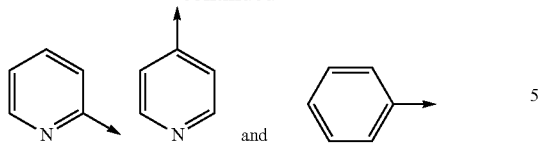

and

V represents —CH$_2$—;
W represents a single bond;
X represents —NH—; and
Z represents —CH$_2$—.

16. A potassium salt according to claim 15, which is selected from the group consisting of:

Potassium, 4-{4-[(4-fluorobenzylamino)methyl]imidazol-1-ylmethyl}benzoate;
Potassium, 4-{4-[(3-methoxybenzylamino)methyl]imidazol-1-ylmethyl}benzoate;
Potassium, 4-{4-[(4-methoxybenzylamino)methyl]imidazol-1-ylmethyl}benzoate;
Potassium, 4-{4-[(3-trifluoromethylbenzylamino)methyl]imidazol-1-ylmethyl}benzoate;
Potassium, 4-{4-[(2-fluoro-4-bromobenzylamino)methyl]imidazol-1-ylmethyl}benzoate;
Potassium, 4-(4-{[(Furan-2-ylmethyl)amino]methyl}imidazol-1-ylmethyl)benzoate;
Potassium, 4-(4-{[(Pyridin-2-ylmethyl)amino]methyl}imidazol-1-ylmethyl)benzoate;
Potassium, 4-(4-{[(Pyridin-4-ylmethyl)amino]methyl}imidazol-1-ylmethyl)benzoate; and
Potassium, 4-[4-(Benzylaminomethyl)imidazol-1-ylmethyl]benzoate.

* * * * *

UNITED STATES PATENT AND TRADEMARK OFFICE
CERTIFICATE OF CORRECTION

PATENT NO. : 8,673,955 B2
APPLICATION NO. : 11/997485
DATED : March 18, 2014
INVENTOR(S) : Carniato et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1527 days.

Signed and Sealed this
Twenty-ninth Day of September, 2015

Michelle K. Lee
*Director of the United States Patent and Trademark Office*